(12) United States Patent
Ziraknejad et al.

(10) Patent No.: US 11,662,830 B2
(45) Date of Patent: *May 30, 2023

(54) METHOD AND SYSTEM FOR INTERACTING WITH MEDICAL INFORMATION

(71) Applicant: NZ Technologies Inc., Vancouver (CA)

(72) Inventors: Nima Ziraknejad, North Vancouver (CA); Pranav Saxena, Vancouver (CA); Anshul Porwal, Surrey (CA)

(73) Assignee: NZ Technologies Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/580,356

(22) Filed: Jan. 20, 2022

(65) Prior Publication Data

US 2022/0147150 A1 May 12, 2022

Related U.S. Application Data

(63) Continuation of application No. 15/775,639, filed as application No. PCT/IB2016/056228 on Oct. 17, 2016, now Pat. No. 11,256,334.

(Continued)

(51) Int. Cl.
*G06F 3/01* (2006.01)
*G06F 3/0354* (2013.01)
(Continued)

(52) U.S. Cl.
CPC .............. *G06F 3/017* (2013.01); *A61B 34/00* (2016.02); *A61B 34/10* (2016.02); *A61B 34/25* (2016.02);
(Continued)

(58) Field of Classification Search
CPC ........ G06F 3/017; G06F 3/044; G06F 3/0481; G06F 3/04815; G06F 3/04817; G06F 3/04883; G06F 3/1415
See application file for complete search history.

(56) References Cited

U.S. PATENT DOCUMENTS

2006/0164230 A1 7/2006 DeWind et al.
2007/0220437 A1 9/2007 Boillot
(Continued)

FOREIGN PATENT DOCUMENTS

JP 2012-526328 A 10/2012
WO 2013093837 A1 6/2013
WO 2014190018 A1 11/2014

OTHER PUBLICATIONS

International Search Report; Canadian Intellectual Property Office; International Application No. PCT/IB2016/056228; dated Jan. 19, 2017; 3 pages.

(Continued)

*Primary Examiner* — William L Bashore
*Assistant Examiner* — Gregory A Distefano
(74) *Attorney, Agent, or Firm* — Todd A. Rattray; Oyen Wiggs Green & Mutala LLP

(57) ABSTRACT

A system for permitting a medical practitioner to interact with medical information, the system including: a sensing unit for detecting a position of a reference object used to interact with the sensing unit; at least one control unit for determining a gesture performed by the medical practitioner, identifying a command relative to the medical information that corresponds to the gesture, and executing the command in order to display the medical information; generating a graphical user interface including a virtual representation of the reference object and at least one virtual icon and/or a virtual representation of the sensing unit, with each of the at least one virtual icon corresponding to one of a respective mode of operation, a respective user notification, and a respective system setting option; and displaying the GUI along with the medical information.

20 Claims, 15 Drawing Sheets

Related U.S. Application Data

(60) Provisional application No. 62/260,428, filed on Nov. 27, 2015.

(51) Int. Cl.

| | | |
|---|---|---|
| *G06F 3/044* | (2006.01) | |
| *G06F 3/04883* | (2022.01) | |
| *A61B 34/00* | (2016.01) | |
| *A61B 34/10* | (2016.01) | |
| *G06F 3/14* | (2006.01) | |
| *G06F 3/04815* | (2022.01) | |
| *G06F 3/0482* | (2013.01) | |
| *G06F 3/0481* | (2022.01) | |
| *G06F 3/03* | (2006.01) | |
| *G06F 3/04817* | (2022.01) | |
| *G16H 40/63* | (2018.01) | |
| *A61B 34/35* | (2016.01) | |
| *G06F 3/04845* | (2022.01) | |

(52) U.S. Cl.
CPC ........ *G06F 3/0304* (2013.01); *G06F 3/03547* (2013.01); *G06F 3/044* (2013.01); *G06F 3/0481* (2013.01); *G06F 3/0482* (2013.01); *G06F 3/04815* (2013.01); *G06F 3/04817* (2013.01); *G06F 3/04883* (2013.01); *G06F 3/1415* (2013.01); *A61B 34/35* (2016.02); *A61B 2034/254* (2016.02); *G06F 3/04845* (2013.01); *G06F 2203/04108* (2013.01); *G09G 2354/00* (2013.01); *G09G 2370/022* (2013.01); *G09G 2380/08* (2013.01); *G16H 40/63* (2018.01)

(56) References Cited

U.S. PATENT DOCUMENTS

| | | | |
|---|---|---|---|
| 2010/0073150 A1* | 3/2010 | Olson | A61B 34/74 340/407.1 |
| 2010/0231509 A1 | 9/2010 | Boillot et al. | |
| 2010/0281440 A1 | 11/2010 | Underkoffler et al. | |
| 2011/0055729 A1 | 3/2011 | Mason et al. | |
| 2012/0131488 A1 | 5/2012 | Karlsson et al. | |
| 2012/0218183 A1 | 8/2012 | Givon et al. | |
| 2014/0085185 A1 | 3/2014 | Sarwar et al. | |
| 2014/0368422 A1 | 12/2014 | Gupta et al. | |
| 2015/0084866 A1 | 3/2015 | Thomas et al. | |
| 2015/0253860 A1 | 9/2015 | Merics et al. | |
| 2015/0355805 A1* | 12/2015 | Chandler | G06F 3/04842 715/784 |
| 2016/0217339 A1 | 7/2016 | Zhao et al. | |
| 2016/0228633 A1 | 8/2016 | Welsch et al. | |
| 2019/0167370 A1 | 6/2019 | Olson | |
| 2020/0193206 A1* | 6/2020 | Turkelson | G06T 1/0014 |

OTHER PUBLICATIONS

Written Opinion of the International Searching Authority; Canadian Intellectual Property Office; International Application No. PCT/IB2016/056228; dated Jan. 19, 2017; 5 pages.

Communication Pursuant to Article 94(3) EPC; European Patent Office; European Patent Application No. 16868102.1; dated Dec. 4, 2018; 7 pages.

Justin H. Tan, MD et al.; Informatics in Radiology, Developing a Touchless User Interface for Intraoperative Image Control during Interventional Radiology Procedures; RadioGraphics; Mar.-Apr. 2013; vol. 33 No. 2; 11 pages.

* cited by examiner

METHOD AND SYSTEM FOR INTERACTING WITH MEDICAL INFORMATION

REFERENCE TO RELATED APPLICATIONS

This application is a continuation of U.S. application Ser. No. 15/775,639 having a filing date of 11 May 2018, which in turn is a § 371 national phase entry of PCT/IB2016/056228 having an international filing date of 17 Oct. 2016, which in turn claims priority (and the benefit under 35 USC § 119) from U.S. application No. 62/260,428 filed 27 Nov. 2015. All of the applications referred to in this paragraph are hereby incorporated herein by reference for all purposes.

TECHNICAL FIELD

The present invention relates to the field of methods and systems for interacting with medical information.

BACKGROUND

There is a desire to provide medical practitioners (e.g. surgeons, interventional radiologists, nurses, medical assistants, other medical technicians and/or the like) with access to the ability to manipulate and/or the ability to otherwise interact with medically relevant information such as prior, during and/or after the performance of medical, surgical, and interventional procedures and/or operations, and/or the like. Such desired medical information may include, by way of non-limiting example, radiological images, angiography images, other forms of images of the patient's body, other information relevant to a patient undergoing a medical procedure, other information relevant to the procedure itself, other information related to the condition being treated and/or the like. Such desired medical information may be procured prior to performing the procedure, during performance of the procedure, and/or after performance of the procedure, and may allow medical practitioners to formulate or alter their therapeutic plan during image-guided and/or image-dependent medical procedures.

Currently, intra-procedural access to, manipulation of and/or interaction with medical information such as radiological images takes place on a computer workstation in a control room located outside of the surgical sterile environment. Such a computer workstation may access, via suitable network communications or other digital access techniques, information such as archives of image data pertaining to a patient by accessing picture archiving and communication systems (PACS); digital imaging and communications in medicine systems (DICOM), hospital information systems (HIS), radiological information systems (RIS) and/or the like. Such workstations may then display individual images on a suitable display and may permit manipulation of the images via a conventional computer-based user interface— e.g. using a mouse and keyboard and a software-implemented user interface. Since the workstation is usually located outside of the surgical sterile environment, a medical practitioner such as a radiologist wanting to access various images typically has to either: (a) scrub out of a procedure on one or more occasions during the procedure; or (b) delegate the task of accessing the desired image(s) to a another person such as a technologist or a nurse, who then has to operate the workstation under the direction of the radiologist.

In case (a), the need for the medical practitioner to move back and forth between the non-sterile control room and the sterile surgical environment for purposes of image navigation and interpretation may: increase the risk of contaminating the sterile environment by inadvertently transferring contaminants from the non-sterile control room into the sterile environment; extend the time required to complete the surgery, thereby increasing procedural costs; and/or interrupt the medical practitioner's cognitive focus, thereby increasing the medical risk for the patient. In case (b), close communication between the radiologists and the technologist operating the workstation is typically required. Communication of relevant information (e.g. how much to move or enlarge an image) is difficult and time-consuming and may require several iterations. This process may be made more difficult by the need to use different software platforms, to navigate through vendor-specific multi-layered menus, and to interact with volumetric images using a keyboard and mouse. In both cases (a) and (b), there are factors that contribute to surgeon's fatigue which is a big problem during surgical and/or interventional procedures.

With an increasing reliance on numerous radiological images for intra-procedural planning and confirmation of targeted therapy, there is a general desire to develop solutions that improve the radiologist's ability to rapidly access, manipulate and/or otherwise interact with large amounts of image information (and/or other medically relevant information) in an intuitive, comprehensive, and timely manner while in the sterile environment.

Therefore, there is a need for an improved method and system for interacting with medical information.

SUMMARY

According to a first broad aspect, there is provided a system for permitting a medical practitioner to interact with medical information, the system comprising: a sensing unit for detecting at least a position of a reference object used by the medical practitioner to interact with the sensing unit; at least one control unit being in communication with the sensing unit for: determining a gesture performed by the medical practitioner using the position of the reference object detected by the sensing unit; identifying a command relative to the medical information that corresponds to the received gesture and executing the command in order to display the medical information on a display unit; generating a graphical user interface (GUI) comprising a virtual representation of the reference object and at least one of a virtual representation of the sensing unit and at least one virtual icon, a position of the virtual representation of the reference object within the GUI being chosen as a function of the position of the reference object detected by the sensing unit, each of the at least one virtual icon corresponding to one of a respective mode of operation, a respective user notification and a respective system setting option; and displaying the GUI on the display unit along with the medical information.

In one embodiment, the controller is configured for displaying the GUI adjacent to the medical information.

In one embodiment, the controller is configured for displaying the GUI and the medical information on a same display device.

In another embodiment, the controller is configured for displaying the GUI and the medical information on separate display devices being positioned adjacent to one another so that the GUI be in a field of view of the medical practitioner when the medical practitioner looks at the displayed medical information.

In one embodiment, the sensing unit is further adapted to detect an orientation of the reference object, an orientation of the virtual representation of the reference object within the GUI being chosen as a function of the orientation of the reference object detected by the sensing unit.

In one embodiment, the sensing unit comprises a single sensor adapted to determine the position and the orientation of the reference object and determine the gesture performed by the medical practitioner.

In one embodiment, the single sensor comprises an optical sensor.

In one embodiment, the optical sensor comprises a camera.

In one embodiment, the camera comprises one of a 3D camera, a stereo camera and a time-of-flight cameras.

In one embodiment, the camera is configured for imaging a reference surface.

In one embodiment, the system further comprises a projector for projecting at least one reference icon on the reference surface imaged by the camera, each one of the at least one reference icon corresponding to a respective one of the at least one virtual icon.

In one embodiment, the reference surface comprises a screen on which at least one reference icon is displayed, each one of the at least one reference icon corresponding to a respective one of the at least one virtual icon.

In another embodiment, the sensing unit comprises a first sensor for determining the position of the reference object and a second sensor for determining the orientation of the reference object, the gesture being determined by one of the first and second sensors.

In one embodiment, the first sensor comprises an electric field sensor for determining the position of the reference object and the second sensor comprises an optical sensor for determining an orientation of the reference object.

In one embodiment, the optical sensor comprises a camera.

In one embodiment, the camera comprises one of a 2D camera, a monochrome camera, a stereo camera and a time-of-flight camera.

In one embodiment, the camera is positioned for imaging a region located above the electric field sensor.

In one embodiment, the system comprises a projector for projecting at least one reference icon on the electric field sensor or around the electric field sensor, each one of the at least one reference icon corresponding to a respective one of the at least one virtual icon.

In one embodiment, the system further comprises a screen on which at least one reference icon is displayed, each one of the at least one reference icon corresponding to a respective one of the at least one virtual icon and the electric field sensor being positioned on the screen.

In one embodiment, the reference object comprises a body part of the medical practitioner.

In one embodiment, the body part comprises one of a hand and at least one finger.

In one embodiment, the reference object is made of one of a conductive material and a semi-conductive material.

In one embodiment, the reference object comprises one of a pen, a stylus, a ball, a ring, and a scalpel.

In one embodiment, the command corresponds to a given known command from a peripheral device connectable to a computer machine.

In one embodiment, the given known command corresponds to one of a mouse command, a foot pedal command, a joystick command, and a keyboard command.

In one embodiment, the medical information comprises a medical image, a 3D model, and any combination or sequence thereof.

In one embodiment, the command relative to the medical information comprises a command that causes a change of at least one characteristic of an already displayed medical image.

In one embodiment, the at least one characteristic comprises at least one of a shape, a size, an orientation, a color, a brightness, text and a contrast.

In one embodiment, the controller is adapted to modify an appearance of one of the at least one virtual icon upon a given selection by the medical practitioner.

According to another broad aspect, there is provided a computer-implemented method for allowing a medical practitioner to interact with medical information, the method comprising: detecting a position of a reference object used by the medical practitioner to interact with a sensing unit; determining a gesture performed by the medical practitioner using the detected position of the reference object; identifying a command relative to the medical information that corresponds to the received gesture and executing the command in order to display the medical information on a display unit; generating a graphical user interface (GUI) comprising a virtual representation of the reference object and at least one of a virtual representation of the sensing unit and at least one virtual icon, the position of the virtual representation of the reference object within the GUI being chosen as a function of the detected position of the reference object, each of the at least one virtual icon corresponding to one of a respective mode of operation, a respective user notification and a respective system setting option; and displaying the GUI on the display unit along with the medical information.

In one embodiment, said displaying the GUI comprises displaying the GUI adjacent to the medical information.

In one embodiment, said displaying the GUI comprises displaying the GUI and the medical information on a same display device.

In another embodiment, said displaying the GUI comprises displaying the GUI and the medical information on separate display devices being positioned adjacent to one another so that the GUI be in a field of view of the medical practitioner when the medical practitioner looks at the displayed medical information.

In one embodiment, the method further comprises detecting an orientation of the reference object.

In one embodiment, said detecting the position and the orientation of the reference object is performed using a single sensor adapted to determine the position and the orientation of the reference object and determine the gesture performed by the medical practitioner.

In one embodiment, said detecting is performed using an optical sensor.

In one embodiment, said detecting is performed using a camera.

In one embodiment, said detecting is performed using one of a 3D camera, a stereo camera and a time-of-flight cameras.

In one embodiment, the camera is configured for imaging a reference surface.

In one embodiment, the method further comprises projecting at least one reference icon on the reference surface imaged by the camera, each one of the at least one reference icon corresponding to a respective one of the at least one virtual icon.

In one embodiment, the reference surface comprises a screen on which at least one reference icon is displayed, each one of the at least one reference icon corresponding to a respective one of the at least one virtual icon.

In another embodiment, said detecting the position of the reference object is performed using a first sensor and said detecting the orientation of the reference object is performed using a second sensor, the gesture being determined using one of the first and second sensors.

In one embodiment, the first sensor comprises an electric field sensor for determining the position of the reference object and the second sensor comprises an optical sensor for determining the orientation of the reference object.

In one embodiment, the optical sensor comprises a camera.

In one embodiment, the camera comprises one of a 2D camera, a monochrome camera, a stereo camera and a time-of-flight camera.

In one embodiment, the method further comprises positioning the camera for imaging a region located above the electric field sensor.

In one embodiment, the method further comprises projecting at least one reference icon on the electric field sensor or around the electric field sensor, each one of the at least one reference icon corresponding to a respective one of the at least one virtual icon.

In one embodiment, the method further comprises displaying at least one reference icon on a screen, each one of the at least one reference icon corresponding to a respective one of the at least one virtual icon and the electric field sensor being positioned on the screen.

In one embodiment, the reference object comprises a body part of the medical practitioner.

In one embodiment, the body part comprises one of a hand and at least one finger.

In one embodiment, the reference object is made of one of a conductive material and a semi-conductive material.

In one embodiment, the reference object comprises one of a pen, a stylus, a ball, a ring, and a scalpel.

In one embodiment, the command corresponds to a given known command from a peripheral device connectable to a computer machine.

In one embodiment, the given known command corresponds to one of a mouse command, a foot pedal command, a joystick command, and a keyboard command.

In one embodiment, the medical information comprises a medical image, a 3D model, and any combination or sequence thereof.

In one embodiment, the command relative to the medical information comprises a command that causes a change of at least one characteristic of an already displayed medical image.

In one embodiment, the at least one characteristic comprises at least one of a shape, a size, an orientation, a color, a brightness, text and a contrast.

In one embodiment, the method further comprises modifying an appearance of one of the at least one virtual icon upon a given selection by the medical practitioner.

In the following, a gesture should be understood as a static gesture or a dynamic gesture. A static gesture is defined as a particular configuration, position and/or orientation of a hand which substantially does not move during a given period of time. For example, a static gesture may consist in a closed first with one raised finger. A dynamic gesture is defined as a motion of a hand during a given period of time. The hand may have a particular configuration, position and/or orientation which may be constant or may vary during the motion of the hand. For example, a dynamic gesture may correspond to a rotation of the index while the other fingers are folded.

BRIEF DESCRIPTION OF THE DRAWINGS

Further features and advantages of the present invention will become apparent from the following detailed description, taken in combination with the appended drawings, in which.

DETAILED DESCRIPTION

Figure 1A:
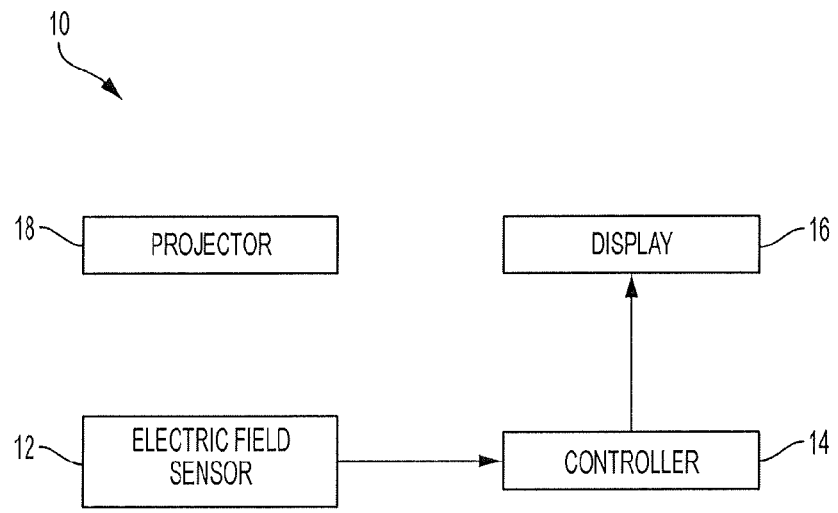
FIG. 1a is a block diagram of a system for interacting with medical information, in accordance with a first embodiment.

The present systems and methods allow a medical practitioner to access, manipulate and/or otherwise interact with medical information via an electric field sensor (e.g. but not limited to an array of capacitive proximity sensors). For example, during a medical procedure, the medical practitioner may use hand or body gestures (e.g. touchless gestures) to interact with the electric field sensor in order to control displayed medical information. The gestures may be based on the configuration, position and/or movement of a practitioner's hand or portion of a hand such as a finger. For example, the gestures may be based on the configuration, position and/or movement of at least one finger of the practitioner's hand. The gestures may be interpreted based on the location/position of the gesture (e.g. the location of the practitioner's hand, finger or fingertip) relative to the electric field sensor. The gestures may additionally or alternatively be based on the configuration or movement of the gesture (e.g. the configuration or movement of the practitioner's hand or finger). Such gesture position, movement or configuration may be relative to the electric field sensor. In another embodiment, the practitioner may hold an object such as an object made of electrically conductive material in his/her hand in order to interact with the electric field sensor. For example, the medical practitioner may hold a pen, a stylus, a metal scalpel, or the like. In this case, the gestures may be based on the configuration, position and/or movement of the object held by the practitioner. The gestures may also be based on the configuration, position and/or movement of the object held by the practitioner and the configuration, position and/or movement of the practitioner's hand that holds the object.

Such systems and methods allow the medical practitioner to interact with medical information or data without the need to scrub out of the sterile environment or to leave the bed (in case of a workstation in the corner of the room) in which the procedure is being performed and without the need to communicate with technicians located outside of the sterile environment. By way of example, medical information or data accessed, manipulated and/or otherwise interacted with during a medical procedure may include: 2D or 3D medical images such as radiological images, angiography images, or other forms of images of the patient's body, medical videos, 2D or 3D images that are not related to the patient's body, information relevant to the patient undergoing the medical procedure, information about the procedure itself, and/or the like. Medical information is displayed to the medical practitioner as a result of the interaction of the medical practitioner with the electric field sensor. The displayed information may comprise 2D/3D images, texts, videos, and/or the like.

In one embodiment, the system may comprise a projection device for projecting a user interface menu image adjacent to the medical practitioner in order to provide visual feedback to the medical practitioner. For example, the user interface menu may be projected adjacent to the electric field sensor or around the electric filed sensor.

The electric field sensor is in communication with a controller which is adapted to translate the gesture performed by the medical practitioner and detected by the electric filed sensor into a command relative to the medical data. In one embodiment, the controller is in communication with a display unit or monitor display. The display unit is adapted to render images such as medical images, images containing text, graphs, drawings, graphics, etc. The display unit may also be used to display videos. The execution of the determined command by the controller causes the display of medical information on the display unit. For example, a first gesture performed by the medical practitioner may command the display of a given medical image while a second and different gesture may command the display of the medical file of the patient. In another embodiment, the controller is in communication with a computer machine that is in communication with the display unit. In this case, the controller is adapted to transmit the command to the computer machine which executes the command in order to display an image on the display.

It should be understood that a video is a sequence of images and that the expression "displaying an image" may be understood as displaying a given image of a video or a video. It should also be understood that an image may only comprise text. Similarly, an image may comprise text, pictures, photographs, drawings, tables, graphics, and/or the like.

In an embodiment in which the system is used during a procedure, based on the interpretation of such gestures, the controller may cause the display unit to render an image (or other information) that is visible to the medical practitioner. The displayed image may comprise an image or a portion of an image from a library of images relating to the patient on whom the procedure is being performed. Based on the interpretation of such gestures, the controller may manipulate the displayed image or display a further image. For example, such manipulation may comprise zooming in or out with respect to a particular displayed image, panning or otherwise moving a displayed portion of a particular displayed image; adjusting brightness, contrast and/or color parameters of a particular displayed image; scrolling through a library of images to select a new image for display; and/or the like.

FIG. 1a illustrates one embodiment of a system 10 for allowing a medical practitioner to interact with medical information. The system 10 comprises at least an electric field sensor or electric field proximity sensor 12 and a controller 14 which is in communication with the electric field sensor 12 for receiving data therefrom.

The electric field sensor is adapted to generate a predefined electric field such as a predefined electromagnetic field or a predefined electrostatic field, and measure the generated electromagnetic field in order to detect and identify a gesture. In an embodiment in which the electric field sensor generates an electric field and when a medical practitioner performs a gesture using his/her hand and/or an object within the electric field, the electric field generated by the electric field sensor is disturbed by the presence of the practitioner's hand and/or the object and the electric field sensor detects the variation of the electric field by comparing the predefined electric field generated by the electric field sensor 12 and the electric field measured by the electric field sensor 12. The variation between the predefined electric field and the measured electric field corresponds to the distortion caused by the gesture of the medical practitioner within the electric field. The electric field sensor 12 is further adapted to determine the gesture that was performed by the medical practitioner from the variation of electric field, and transmit the determined gesture to the controller 14.

It should be understood that any adequate electric field sensor may be used. For example, an electric field sensor comprising an array of capacitive proximity sensors may be used. In another example, the electric field sensor may include an array of electrodes.

In one embodiment, the gesture outputted by the electric field sensor 12 corresponds to the 2D or 3D position of the hand of the medical practitioner such as the 2D or 3D position of a given point of the hand as a function of time. For example, the position of the hand may be defined as the point of the hand that is the closest to the electric field sensor 12. For example, the gesture may correspond to the 2D or 3D position of a fingertip. In another example, the gesture may correspond to the 2D or 3D position of the fingertip of more than one finger. In a further example, the gesture may correspond to the 2D or 3D position of the tip of an object hold by the medical practitioner. It should be understood that a position may also refer to a variation of position.

In another embodiment, the gesture outputted by the electric field sensor 12 corresponds to the determined variation of electric field that occurs when the medical practitioner performs a gesture within the electric field generated by the electric field sensor 12. In this case, the controller 14 is adapted to determine the gesture performed by the medical practitioner from the variation of electric field received from the electric field sensor 12.

In one embodiment, the gesture outputted by the electric field sensor 12 corresponds to a discrete input for the controller 14. In this case, the gesture performed by the medical practitioner is substantially static, i.e. the medical practitioner positions his/her hand, his/her finger, and/or an object at a fixed position within the electric field for a given period of time. For example, a static gesture may correspond to a position represented by coordinates (X, Y, Z). In another example, a static gesture may correspond to a variation of position expressed by (.delta.X, .delta.Y, .delta.Z).

In another embodiment, the gesture outputted by the electric field sensor 12 corresponds to a continuous input for the controller 14. In this case, the gesture performed by the medical practitioner is continuous or dynamic, i.e. the medical practitioner substantially continuously moves his/her hand, his/her finger, and or an object within the electric field during a given period of time. For example, a continuous or dynamic gesture may be represented by coordinates as function of time (X(t), Y(t), Z(t)).

The controller 14 is adapted to receive the gesture from the electric field sensor 12 and determine a command or action to be executed. The command to be executed is related to medical information. The controller 14 accesses a database in order to determine the command to be executed. The database comprises a set of commands to be executed and each command is associated with a respective predefined gesture. Each command is related to medical information, and more particularly to the display, modification, and/or selection of medical information. Therefore, the controller 14 is adapted to retrieve the command to be executed by comparing the received gesture to the predefined gestures stored in the database. When the received gesture matches a given predefined gesture, the controller 14 identifies the command to be executed as being the command that corresponds to the given predefined gesture. For example, the execution of a first command may cause text containing medical information about a patient to be displayed. In another example, the execution of a second command may cause a medical image to be displayed. In a further example, the execution of a third command may cause the rotation of a displayed medical image. In still another example, the execution of a fourth command may cause a zoom on a medical image.

In an embodiment in which a gesture outputted by the electric field sensor 12 corresponds to a discrete position such as coordinates (X, Y, Z) or a continuous position such as coordinates (X(t), Y(t), Z(t)), the database comprises a set of predefined commands to be executed and each command is associated with a respective predefined discrete position or a respective predefined sequence of positions. In this case, the controller 14 is configured for comparing the received position to the set of positions stored in the database and identifying the command to be executed as being the predefined command associated with the predefined position that matches the received position.

In an embodiment in which the gesture outputted by the electric field sensor 12 corresponds to a variation of electric field, the database comprises a set of predefined commands to be executed and each command is associated with a respective predefined variation of electric field. In this case, the controller 14 is adapted to retrieve the command to be executed by comparing the received variation of electric field to the predefined variations electric field stored in the database. When the received variation of electric field matches a given predefined variation of electric field, the command corresponding to the given predefined variation of electric field is identified as being the command to be executed. The commands stored in the database are related to medical information.

In one embodiment, the database of predefined commands and corresponding gestures is stored locally on the controller 14. In another embodiment, the database of predefined commands is stored externally and the controller is in communication with the computer machine on which the database is stored.

As illustrated in FIG. 1a, the controller 14 is in communication with a display unit 16. The display unit 16 is adapted to display texts, graphs, images such as medical images, videos thereon. Once the command to be performed has been identified, the controller is adapted to execute the command. The execution of the command causes the display unit 16 to display an image or a portion of an image comprising medical information. As described above, the displayed image may comprise text such as information related to the patient. In another example, the displayed image may correspond to a medical image. In one embodiment, the controller 14 is in communication with at least one computer machine on which a medical database is stored. The medical database comprises medical information such as medical images, medical videos, medical information (e.g. patient files), and/or the like.

In one embodiment, the system 10 further comprises a projector 18 for projecting a user interface menu image or other useful graphics on a surface. The menu image may comprise at least one icon each representing a different mode of operation for the system 10. In one embodiment, the menu image is projected on and around the electric field sensor 12 so that the icons be positioned adjacent the electric field sensor 12. In another embodiment, the menu image may be projected away from the electric field sensor 12. In one embodiment, the projector is independent from the controller 16. In another embodiment, the projector is in communication with and controlled by the controller 16. In this case, the projector may project images representing icons adjacent the electric field sensor 12. For example, each icon may represent an operation mode for the system 10 and the controller 16 may be adapted to set the color of a given icon that corresponds to the actual mode of operation to a given color in order to provide a visual feedback to the medical practitioner. For example, all icons may be white and when the medical practitioner selects a given operation mode by interacting with the electric field sensor 12, the controller changes via the projector the color of the icon that corresponds to the selected operation mode. For example, the color of the icon corresponding to the selected operation mode may be changed to yellow.

Figure 1B:
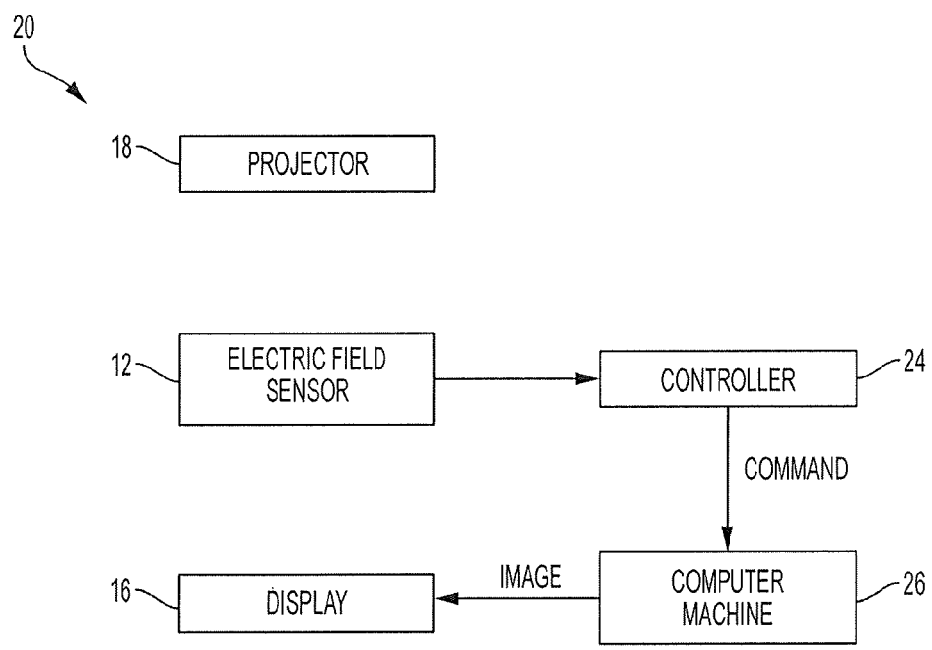
FIG. 1b is a block diagram of a system for interacting with medical information, in accordance with a second embodiment.

While the controller 14 is connected to the display unit 16 and is adapted to execute the command determined according to the detected gesture, FIG. 1*b* illustrates one embodiment of a system 20 for interacting with medical information in which a controller 24 is adapted to transmit commands to a computer machine 26 that is connected to the display unit 16. In this case, the controller is adapted to receive the gesture from the electric field sensor 12 and determine the command that corresponds to the received gesture, as described above with respect to the controller 14. However, the command is then sent to the computer machine 26 that is adapted to execute the command in order to display medical information of the display unit 16. In this case, the controller 16 may be seen as an interface between the electric field sensor 12 and the computer machine 26. The controller 24 is adapted to convert a gesture detected by the electric field sensor 12 into a command that is known and understood by the computer machine. For example, the controller 24 may convert gestures detected by the electric field sensor 12 into a command that would be generated by a computer peripheral such as a mouse command (such as a left or right click or a double click) or into a keyboard command. The computer machine 26 then executes the command received from the controller 24 as if the command would have been received from a peripheral that is connected to the computer machine 26.

In one embodiment, the system 10 is used during a medical procedure on a patient. In this case, the electric field sensor 12, the controller 14, the display unit 16, and the projector 18, if any, are located in the sterile environment in which the procedure is performed. The controller may be in communication with the computer machine of the control room workstation located in the control room which corresponds to a non-sterile environment. The control room workstation may be in communication with servers on which medical images and medical information about patients are stored. When a command identified by the controller 14 corresponds to displaying a medical image or medical text, the controller 14 sends to the control room workstation a request indicative of the medical image or the medical information to be retrieved. The control room workstation communicates with the adequate server to retrieve the information requested by the controller 14. Upon receiving the requested medical image or medical text, the control room workstation transmits the received data to the controller 14 which locally stores the received medical image or text in order to display it on the display unit 16.

The same may apply to the system 20 illustrated at FIG. 1*b*. In this case, the computer machine 26 may correspond to the control room workstation 26 and the controller 24 is adapted to convert the gestures received from the electric field sensor 12 into commands to be transmitted to the control room workstation 26 that executes the commands.

In the following, there is described an exemplary system 50 allowing a medical practitioner to interact with medical information during a medical procedure.

Figure 2:
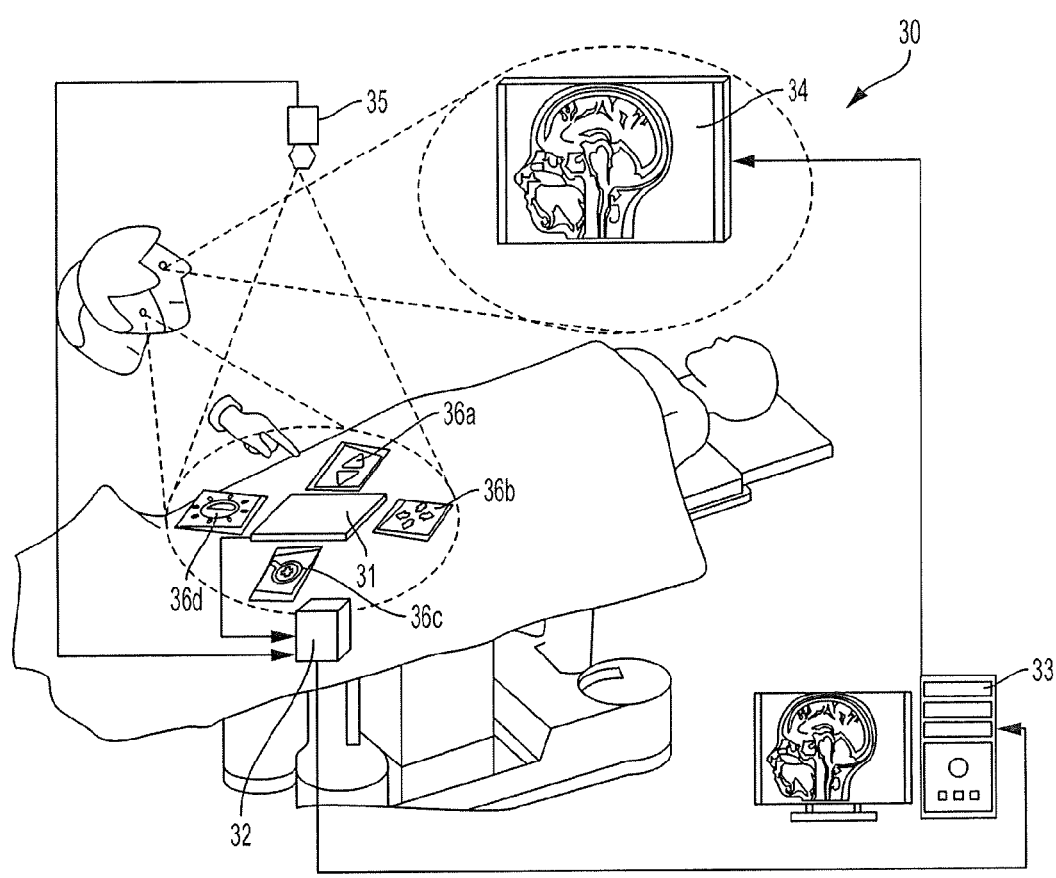
FIG. 2 illustrates a system for interacting with medical information, comprising a projector for displaying a user interface on or around an electric field sensor, in accordance with an embodiment.

As described above, the system may comprise a projector for projecting a user interface menu image. FIG. 2 illustrates one embodiment of a system 30 comprising an electric field sensor 31, a controller 32, a computer 33, a display unit 34 and a projector 35. The controller 32 is in communication with the electric field sensor 31 and the projector 35. The projector 35 is adapted to project a user interface menu image which comprises four icons 36*a*, 36*b*, 36*c* and 36*d* which each represent a mode of operation for the system 30. The electric field sensor 31 is positioned by the medical practitioner on the patient (as illustrated) or adjacent to the bed on which the patient lies.

In one embodiment, the controller 32 is adapted to change the appearance of the four icons 36*a*-36*d* in order to provide the medical practitioner with a visual feedback on the actual operation mode of the system 30, as described below. For example, the controller 32 may change the color and/or shape of the icon representing the actual mode of operation.

Figure 3:
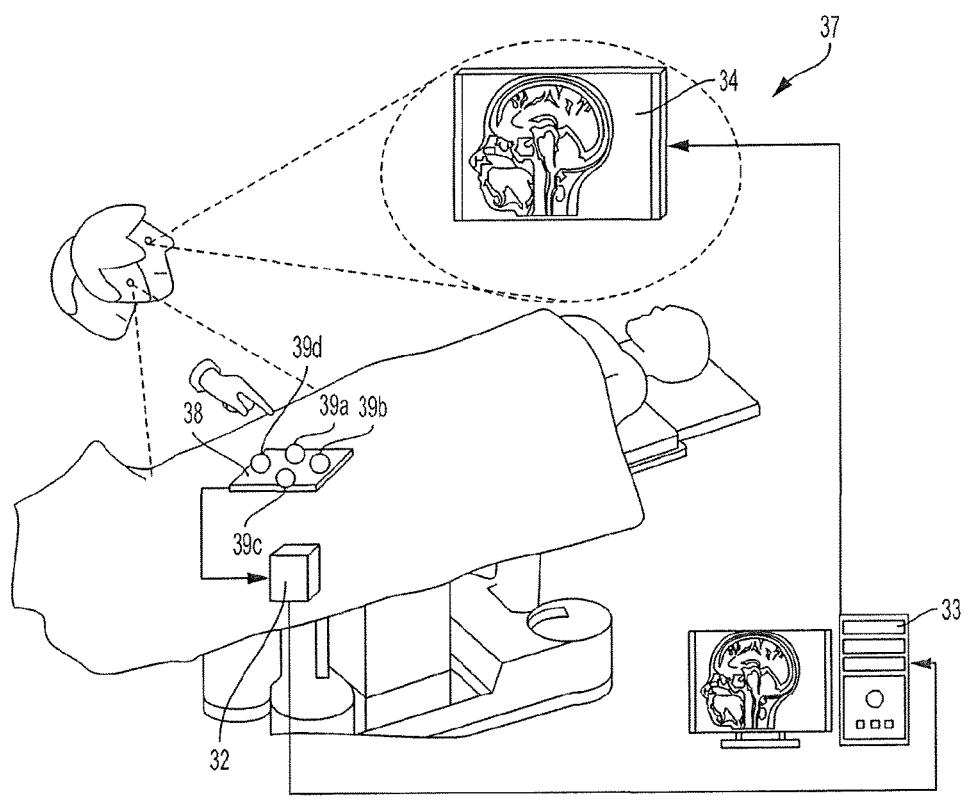
FIG. 3 illustrates a system for interacting with medical information, comprising a sensor having displays integrated thereon for displaying icons, in accordance with an embodiment.

FIG. 3 illustrates one embodiment of a system 37 comprising an electric field sensor 38, a controller 32, a computer 33, and a display unit 34. The electric field sensor 38 comprises four displays 39*a*, 39*b*, 39*c*, and 39*d* integrated on the top surface thereof. The controller 32 is adapted to display icons on each display 39*a*-39*d*, each icon representing a respective mode of operation for the system.

In one embodiment, the controller 32 is adapted to change the appearance of the four icons displayed on the displays 39*a*-39*d* in order to provide the medical practitioner with a visual feedback on the actual operation mode of the system 37. For example, the controller 32 may change the color, brightness, and/or shape of the icon representing the actual mode of operation.

Figure 4:
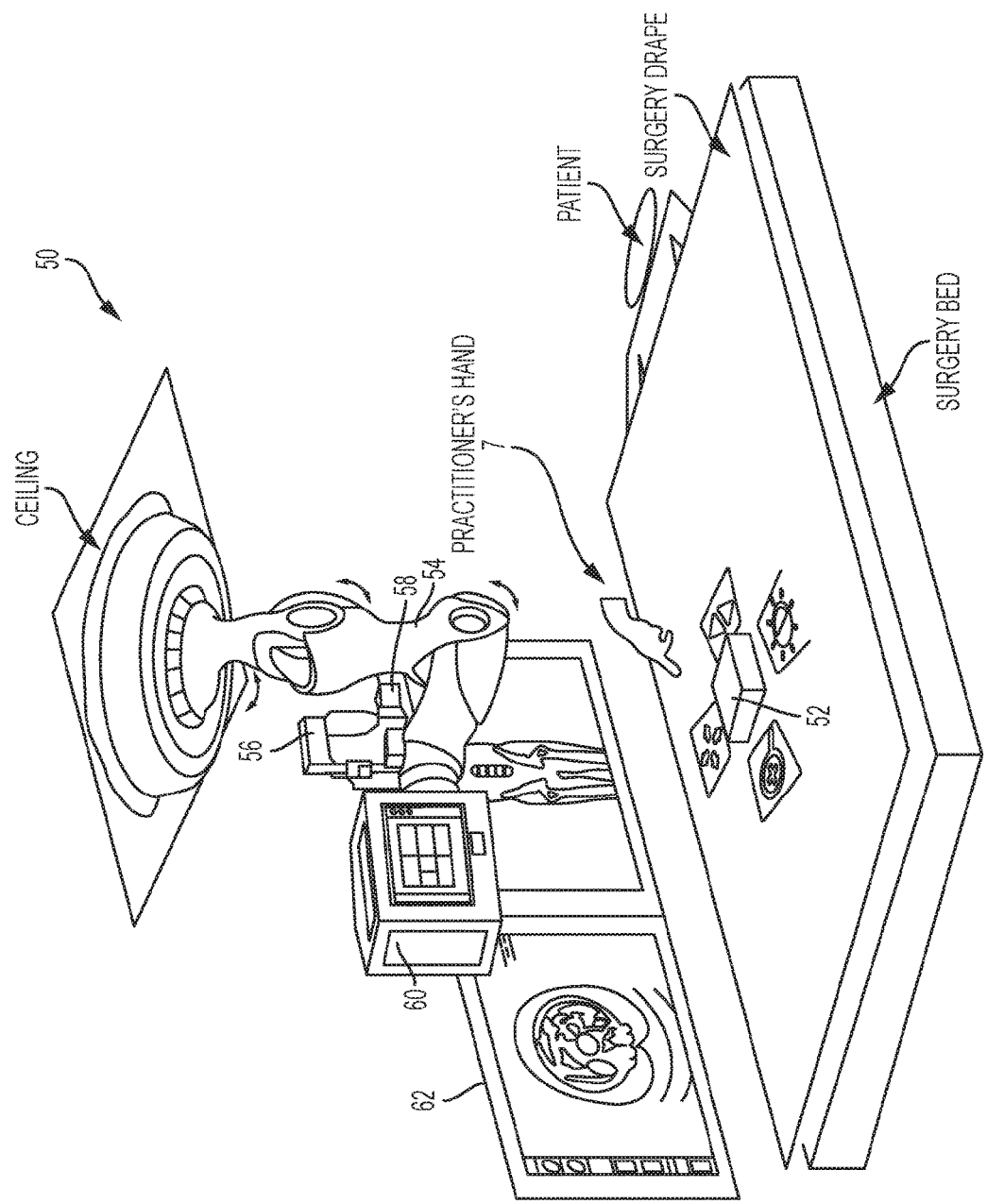
FIG. 4 illustrates a system for accessing medical information comprising a robotic arm, in accordance with an embodiment.

FIG. 4 illustrates a system 50 that comprises an electric field sensor 52 adapted to detect hand and body gestures performed by a medical practitioner, an articulated robotic arm 54 having at least two degrees of freedom (DOF) (not shown), a visual feedback system (VFS) 56 such as an overhead optical projector for projecting a menu image, an optical 2D or 3D position tracking device 58 such as a monochrome camera or a time-of-flight camera, for tracking the position of the electric field sensor 52, a controller or embedded computer 60, and a display monitor 62 for displaying medical information such as medical images.

Figure 5:
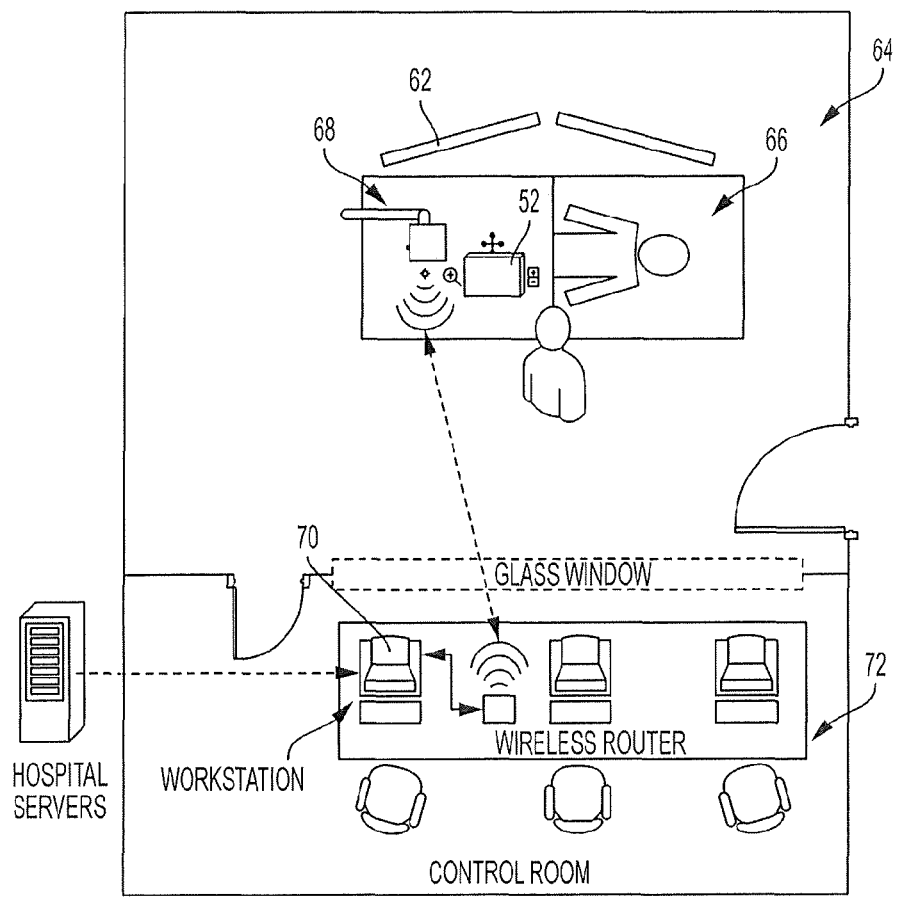
FIG. 5 schematically illustrates an operating room in which the system of FIG. 3 is installed, and a control room, in accordance with an embodiment.

In one embodiment, the system 50 is used during a medical procedure in an operating room 64 as illustrated in FIG. 5. In one embodiment, the medical practitioner divides his/her workspace on a surgery bed in two sections: a first section 66 where a medical procedure on a patient's body is to be conducted, and a second section 68 which corresponds to the rest of the surgery bed, which is intended for placing various medical/surgical tools for quick access. For example, as illustrated in FIG. 4, the lower torso/leg area of the patient on the surgery bed is being used for placement of tools, including the electric field sensor 52. This location for the electric field sensor 52 enables the surgeon to have easy control over medical images displayed on the monitor 62 from the surgery bed. This arrangement also allows the medical practitioner not to have to exit the operating room in order to use the control room workstation 70 located in an adjacent non-sterile control room 72, and come back into the operating room to continue with the medical procedure.

In one embodiment, the electric field sensor 52 is inserted into a sterile bag or container such as a disposable sterile bag so that the electric field sensor may be used from one surgery to another. In another embodiment, the electric field sensor 52 is made disposable and may be thrown away after a single use during a surgery.

In the illustrated embodiment, the electric field sensor 52 is positioned on a receiving surface which is the surgery bed in this case. The motorized robotic arm 54 has a first end secured to the ceiling of the procedure room and the surgery bed is located within the procedure room so as to be under the motorized robotic arm 54. The controller 60 is secured at the second end of the robotic arm 54. The VFS 56 is secured to the robotic arm 54 adjacent to the controller 60. The tracking device 58 is secured to the VFS 56.

The controller 60 is in communication with the electric field sensor 52, the robotic arm 54, the VFS 56, and the tracking device 58. In one embodiment, the system 50 is located in a sterile environment such as an operating room and the controller 60 is further in communication with a workstation located in a non-sterile control room which is adjacent to the sterile room. The workstation may comprise medical information stored thereon and/or be in communication with at least one server on which medical information is stored, such as Picture Archiving and Communication System (PACS) servers.

It should be understood that any adequate communication methods may be used. For example, wired communication may occur between some of the components of the system 50 while wireless communication, such as Wi-Fi, Bluetooth or Ethernet communication, may occur between other components of the system 50.

Figure 6:
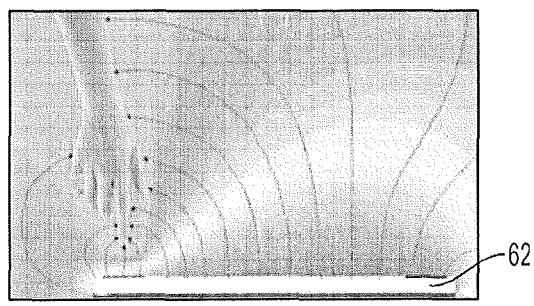
FIG. 6 illustrates an interaction between a hand and an electric field generated by an electric field sensor, in accordance with an embodiment.
Figure 7:
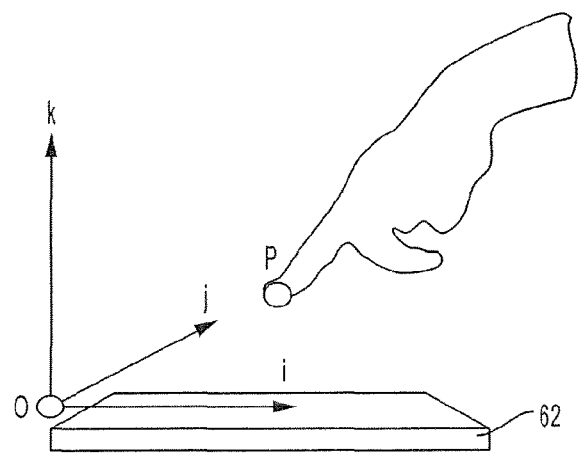
FIG. 7 illustrates the position of a fingertip relative to an electric field sensor, in accordance with an embodiment.

In the illustrated embodiment, the electric field sensor 52 is a self-contained rectangular pad adapted to generate a pre-calibrated electric field envelope over its surface for short range 3D sensing. When an object such as a hand is placed above the pad within the generated electric field, a distortion occurs in the generated electric field and part of the generated electric field is shunted to the ground, as illustrated in FIG. 6. The electric field sensor 52 comprises an array of electrodes that independently measure the disturbance induced by the object in the generated electric field by detecting the change in capacitance values that are measured individually. The electric field sensor 52 is further adapted to determine the 2D or 3D position of the object that generated the disturbance using the changes in capacitance measured by the electrodes. For example, the electric field sensor 52 may be adapted to calculate the 3D position of a fingertip P with respect to an origin O of the sensor's base coordinate frame, as illustrated in FIG. 7. The electric field sensor 52 is further adapted to transmit in substantially real time the determined gesture, i.e. the determined position, to the controller 60.

The controller 60 is adapted to receive the determined gesture from the electric field sensor 52 and determine a corresponding command to be executed. The controller 60 accesses a database containing a set of predefined gestures and a respective command for each predefined gesture. By comparing the received gesture to the set of predefined gestures stored in the database, the controller 60 identifies the given predefined command to be executed. The controller 60 then executes the command corresponding to the received gesture and displays the medical information resulting from the executed command on the display monitor 62.

In one embodiment, the command to be executed requires medical information stored on the workstation or a PACS server. In this case, the controller 60 communicates with the workstation located in the non-sterile control room to obtain the medical information. Once received, the controller 60 executes the identified command such as displaying medical information received from a PACS server via the workstation. In this case, the command to be executed may comprise an Application Programming Interface (API) message In another embodiment, the command to be executed does not require any communication with the workstation located in the non-sterile control room. In this case, the controller 60 simply executes the identified command. In this case, examples of commands may comprise zooming on an already displayed medical image, rotating an already displayed medical image, etc. In one embodiment, commands not requiring any communication with the workstation located in the control room may correspond to a mouse command or a keyboard command that would usually be performed on the workstation. In such an embodiment, the controller may be provided with a display integrated therein to display the images.

As described above, the system 50 comprises the VFS 56 which is adapted to project a menu image on a surface such as on the surgery bed. In the illustrated embodiment, the menu image comprises four icons spaced apart from another so that the electric field sensor be positioned between the icons substantially at the center of the menu image. Each icon represents a different mode of interaction or operation of the controller 60. The controller 60 is further adapted to control the VFS 56. For example, the controller 56 may change the color of the icon that corresponds to an actual mode of operation to identify the actual mode of operation for the medical practitioner, thereby providing feedback to the medical practitioner. Examples of operation modes may comprise a zoom mode in which a medical practitioner may zoom in or out in an image, a motion mode in which the medical practitioner may move an image, a scroll mode in which the medical practitioner may scroll in a menu, through a series of images, through a sequence of image slices, or the like, a window level mode in which the medical practitioner may adjust the brightness and/or the contrast of a displayed image, a pan mode allowing the medical practitioner for image panning, an image changing mode in which the medical practitioner may switch between images or sets of images, an image reset mode or command for transforming an image back to its default configuration, an autoplay command or mode for starting automatic cycling through a series of images or videos in a given sequence, a file editing mode in which functions such as copying, pasting, cutting and the like may be accessed, an image manipulation mode in which manipulations of images such as merger of at least two images may be performed, a feature marker placement mode in which placement of markers that correspond to a particular set of desired features in a set of medical data for easy navigation, etc.

For example, when in the window level mode, a particular position of hand along x-axis may correspond a particular brightness level and the position along y-axis affect the contrast level. When in the image changing mode and if a practitioner has MRI scans (where each scan consists of a series of images) for three different patients, a double air tap gesture may be used as an image changing command to cycle between scans of the three different patients. When in the autoplay command, a medical practitioner may animate and cycle through sets of images in an MRI scan to better understand the anatomy of the scanned organ in a quick manner for example.

When in the image manipulation mode, an air tap gesture may be used to select two images from an X-Ray scan and CT scan for superimposition for example. Once the selection is completed, a left swipe may impose one image over the other so that the medical practitioner may concurrently observe details of both images. When in the feature marker placement mode, a feature may refer to any distinguishing character in the image, such as the position of a certain vein in an image or the position of a particular image in a series of images. For example, when scrolling through a series of images, a medical practitioner may mark images to refer repeatedly by an air tap. Henceforth, he could access the marked images back and forth by left and right swipes respectively.

In an embodiment in which the system 50 comprises more than one mode of interaction or operation, the controller 60 may be adapted to identify two types of gestures. The gestures of the first type may be used for activating a desired mode of operation or passing from one mode of operation to another. In an example in which two modes of operations exist, a single gesture may be used for passing from one mode to the other. For example, when performing the single gesture allows to pass from the first mode to the second mode. Performing the same gesture a second time allows passing from the second mode back to the first mode. In another example, a first gesture may be used to activate the first mode while a second and different gesture may be used for activating the second mode. The second type of gestures that may be performed activates commands once a given mode of operation has been activated. The gestures of the second type may be different from the gestures of the first type. A same gesture may be used in different modes of operation. However, the commands activated by the same gesture in the different modes of operation will trigger different commands. For example, a given gesture may allow zooming in in a zoom mode and the same given gesture may allow increasing the brightness of a displayed image in a brightness mode. Alternatively, the gestures may be unique so that no identical gestures may be used in different modes of operation.

As described above, the system 50 further comprises a position tracking device 58 which is in communication with the controller 60. The position tracking system 58 is adapted to detect the presence of an object and determine the position of the object. The position tracking system is further adapted to transmit the position of the object to the controller 60 which is adapted to control the position and configuration of the articulated robotic arm 54. In one embodiment the object tracked by the position tracking system is the electric field sensor 52. In this case, the controller 60 is adapted to ensure that the icons projected by the VFS 56 remain positioned around the electric field sensor 52 when the position of the electric field sensor 52 is changed. In this case, the controller 60 may be adapted to use the received position of the electric field sensor 52, determine an adequate position for the VFS 56 for ensuring that the icons be positioned around the electric field sensor located at the new position, determine the configuration of the robotic arm 54 in order to position the VFS at the adequate position, and modify the configuration of the robotic arm 54 according to the determined configuration.

In one embodiment, the system 50 further comprises a speaker in order to provide an audio feedback to the medical practitioner. In this case, the VFS 56 may or may not be omitted.

In one embodiment, the VFS 56 may be replaced by a display adapted to display icons representative of the possible operation modes. In this case, the electric field sensor 52 may be positioned or secured to the display so that the icons displayed on the display be located on or around the electric field sensor 52. The controller 60 is then adapted to control the display. For example, the controller may change the appearance of the icon that corresponds to the actual mode of interaction, such as the color and/or shape of the icon, thereby providing feedback to the medical practitioner. In a further embodiment, a receiving surface having icons printed thereon may be used to help the medical practitioner. In this case, the electric field sensor 52 may be secured to the receiving surface or simply positioned thereon. The icons are located on the receiving surface so as to position around the electric field sensor 52. For example, the receiving surface may be a substantially rigid plate, a piece of fabric to be deposited on the surgery bed, etc.

In a further embodiment, the VFS 56 may be omitted and the controller may display the menu icons representative of the different modes of operation directly on the display unit 62.

In the following, there is presented some exemplary gestures that may be used to have commands executed. A first exemplary gesture may correspond to a swipe gesture. Performing a sweeping motion using a fingertip or a hand from one edge of the electric field sensor 52 to an opposite edge may be associated with a given command. In one embodiment, four swipe gestures may be recognized by the controller 60 and each associated with a respective command: swipe from left to right, swipe from right to left, swipe from top to bottom, and swipe from bottom to top. For example, swiping from top to bottom may be associated with passing from one first mode of interaction to a second mode of interaction while swiping from bottom to top may be associated with passing from the second mode of operation back to the first mode of operation. In the same or another example, swiping from left to right may be associated with passing from a first medical image to a second medical image while swiping from right to left may be associated with passing from the second medical image back to the first medical image.

Figure 8:
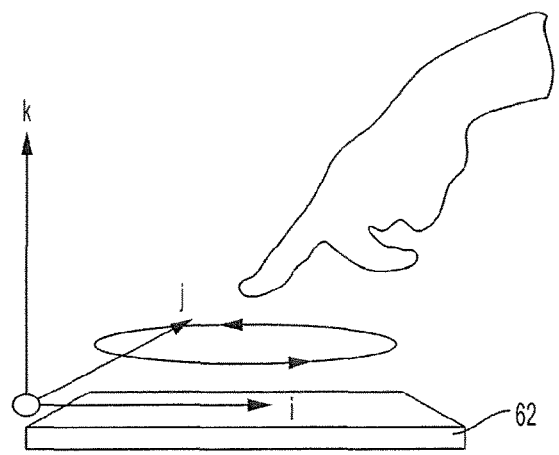
FIG. 8 illustrates an air wheel gesture, in accordance with an embodiment.

A second exemplary gesture corresponds to an air-wheel gesture as illustrated in FIG. 8. Using a fingertip or a hand, the medical practitioner performs a circular motion in a plane substantially parallel to the surface of the electric field sensor 52. This circular motion provides a counter which is increased or decreased according to its motion direction, i.e. clockwise or counter-clockwise. For example, an air-wheel gesture may be used by the medical practitioner to scroll in a drop-down menu to select an image to be displayed.

A third exemplary gesture may correspond to an air tap gesture. An air tap gesture is performed by having the medical practitioner bringing his/her fingertip down towards the electric field sensor 52 and then bringing it back up quickly. The medical practitioner may or may not touch the electric field sensor 52 while executing an air tap gesture. An air tap gesture may be associated with a left click command of a mouse for example.

Another exemplary gesture may correspond to a double air tap. A double air tap is performed by having the medical practitioner executing two air taps successively in a short period of time. For example, a double air tap may be associated with the same command as that associated with a double left click of a mouse. While an air tap refers to a touchless use of the electric field sensor 52, it should be understood that a gesture may include touching the surface of the electric field sensor 52. For example, touching the surface of the electric field sensor 52 may correspond to a mouse click.

While in the illustrated embodiment, it is secured to the robotic arm 54, it should be understood that the controller 60 may be positioned at any other adequate location as long as it remains in communication with at least the electric field sensor 52. Similarly, the electric field sensor 52 may be positioned at any adequate location within the operating room.

Figure 9A:
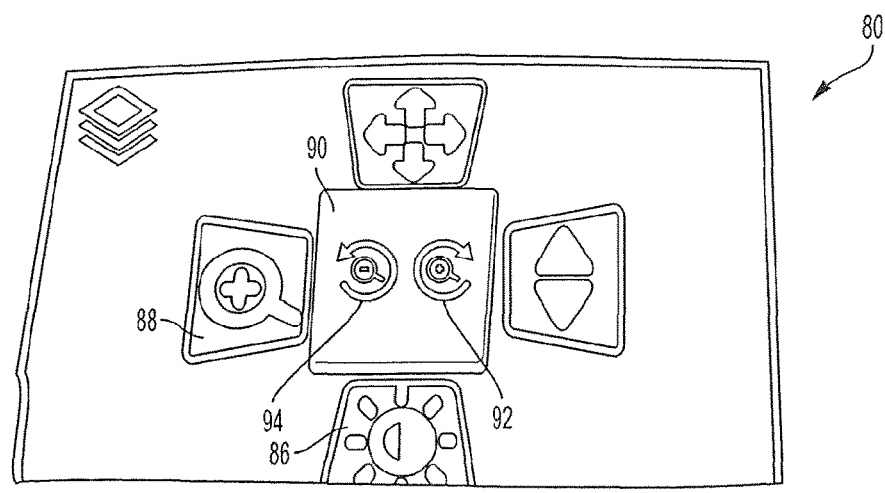
FIG. 9a illustrates one exemplary menu image.

FIG. 9a illustrates one exemplary menu image 80 that may be displayed by a projector such as the VFS 56. The menu image 80 comprises four icons 82-88 which each corresponds to a respective mode of interaction. The menu image 80 is substantially centered on an electric field sensor 90 so that the icons 82-88 be positioned around the electric field sensor 90. As a result, the icon 82 is located on top of the electric field sensor 90, the icon 84 is located on the right of the electric field sensor 90, the icon 86 is located below the electric field sensor 90, and the icon 88 is located on the left of the electric field sensor 90.

Figure 9B:
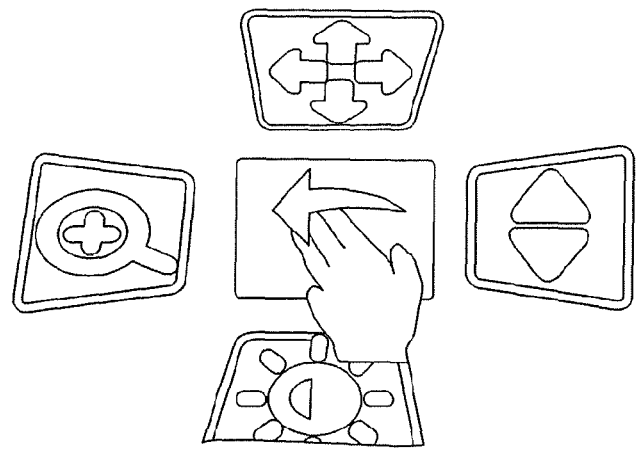
FIG. 9b illustrates a left swipe gesture performed by a medical practitioner, in accordance with an embodiment.
Figure 9C:
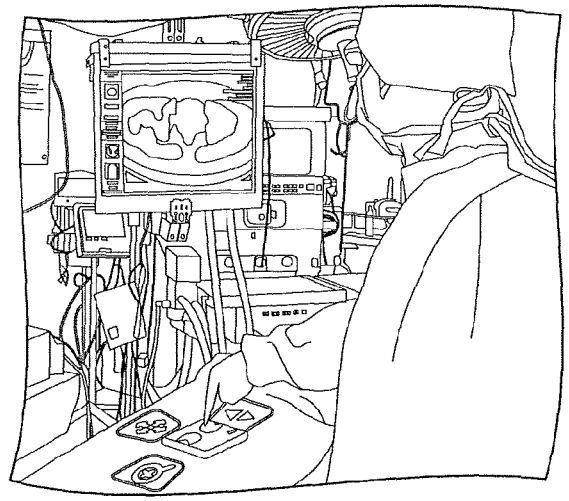
FIG. 9c illustrates an air-wheel gesture performed by a medical practitioner, in accordance with an embodiment.

In one embodiment, a given mode of interaction is activated by performing a swipe gesture in direction of the icon 82-88 corresponding to the desired mode of interaction. For example, a medical practitioner may desire to zoom in a displayed medical image and the icon 88 may be associated with the mode of interaction allowing the medical practitioner to zoom in the displayed medical image. In this case, the icon 88 is referred to as a zoom icon. FIGS. 9b and 9c illustrates a method for activating the zoom mode by performing a swipe in the direction of the icon corresponding to the desired mode of interaction. In the illustrated example, the medical practitioner performs a swipe gesture in order to activate the zoom mode of operation represented by the zoom icon 88. In FIG. 9b, the medical practitioner positions his/her hand on top of the electric field sensor 90 adjacent to the right end of the electric filed sensor 90 and performs a left swipe gesture by moving his/her hand towards the left, i.e. towards the zoom icon 88 corresponding to the desired mode of interaction. The left swipe gesture is detected by the electric field sensor 90 and a signal indicative of the determined gesture is sent by the electric field sensor 90 to the controller such as controller 60. The controller then determines that the operation mode of interaction that corresponds to the left swipe gesture and activates the corresponding mode of interaction.

In another example, the medical practitioner may activate the panning interaction mode by performing an up swipe gesture, i.e. a swipe gesture from bottom to top towards icon 82. Once in the panning interaction mode, changing the position of the practitioner's hand in a 2D plane above the electric field sensor 90 results in image panning.

In one embodiment, upon activation of a given mode of interaction, the controller may modify the menu image by modifying the appearance of the icon corresponding to the activated mode of interaction, as described above.

In the same or another embodiment, the controller may modify the displayed menu image by adding and/or removing displayed icons. For example and as illustrated in FIG. 9a, the controller may add two icons 92 and 94 in the projected menu image 80 upon activation of the zoom interaction mode following the left swipe gesture of the medical practitioner. In the illustrated embodiment, the icons 92 and 94 are positioned within the menu image 80 so as to be projected on the electric field sensor 90. The icons 92 and 94 are designed to guide the medical practitioner to interact with the controller while in the zoom interaction mode. The icon 92 represents a clockwise oriented arrow in which a "+" sign is inserted, which indicates to the medical practitioner that a zoom-in may be done in a displayed image performing a clockwise air-wheel gesture. The icon 94 represents an anticlockwise oriented arrow in which a "−" sign is inserted, which indicates to the medical practitioner that a zoom-out may be done in a displayed image performing an anticlockwise air-wheel gesture. In order to perform an air-wheel, the medical practitioner points a fingertip towards the electric field sensor 90, as illustrated in FIG. 9c, and moves his/her fingertip to perform a circular or semicircular movement.

Figure 9D:
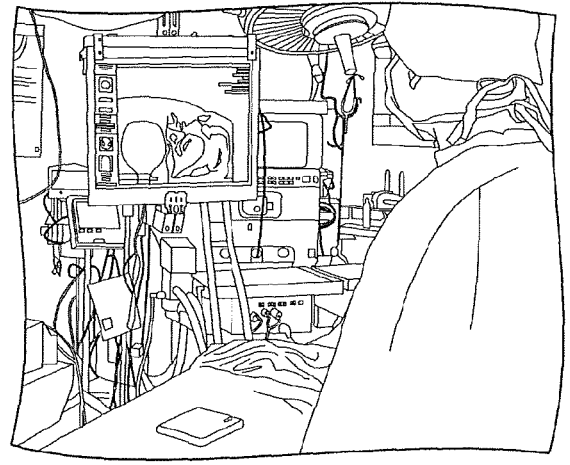
FIG. 9d illustrates a deactivation of an electric field sensor, in accordance with an embodiment.

Once he has performed his/her desired action, the medical practitioner moves his/her hand away from the electric field sensor 90 and after a predefined period of time, the electric field sensor 90 deactivates, as illustrated in FIG. 9d. Once deactivated, the electric field sensor 90 ignores any movement of object that it may detect until reactivation. For example, the electric field sensor 90 may be reactivated by holding an object such as a hand above its surface at a substantially constant position for predefined period of time. It should be understood that any adequate gesture may be used for activating or deactivating the electric field sensor 90.

In an embodiment in which a robotic arm is used to control the position of a projector relative to that of the electric field sensor in order to project a menu image on and around the electric field sensor, the robotic arm allows maintaining the projected menu image on the electric field sensor when the position of the electric field sensor is changed. In addition to ensuring that the menu image will substantially always be projected on the electric field sensor, this further ensures that the projector will substantially always be located above the electric field sensor without obstructing the view of the medical practitioner who will always be allowed to see the displayed image.

Figure 10A:
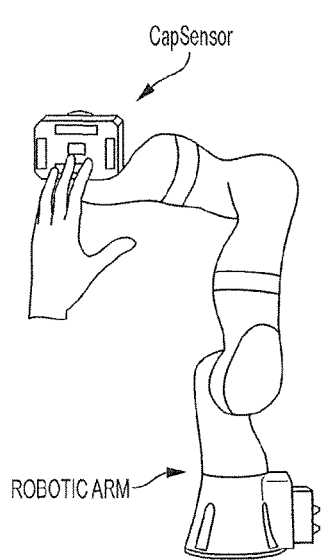
FIG. 10a illustrates an electric field sensor secured to a robotic arm being in a first configuration, in accordance with an embodiment.
Figure 10B:
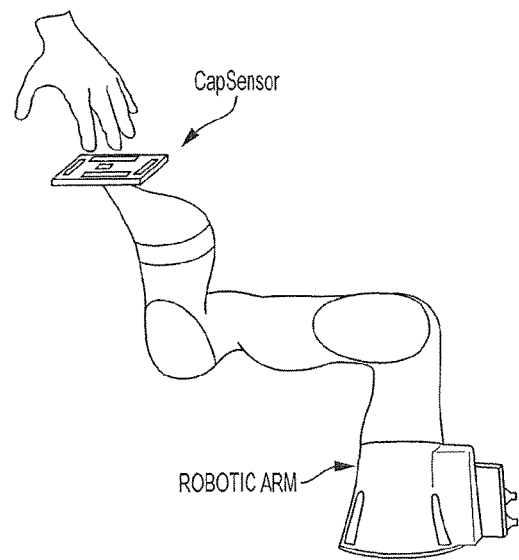
FIG. 10b illustrates the robotic arm of FIG. 9a in a second and different configuration, in accordance with an embodiment.

In an embodiment in which a robotic arm is present, the electric field sensor may be mounted on the robotic arm as illustrated in FIG. 10a. In this case, a display positioned adjacent to the electric field sensor may surround the electric field sensor in order to display menu icons around the electric field sensor. Alternatively, a display may be positioned adjacent to the electric field sensor in order to display menu icons. In such an embodiment, a position tracking device such as device 58 may be present in order to track the position of the medical practitioner such as the position of a hand of the medical practitioner and the controller may be adapted to control the configuration of the robotic arm in order to position the electric field sensor at a given distance from the medical practitioner or the hand of the medical practitioner, as illustrated in FIG. 10b. In this case, the electric field sensor may always be easily accessible for the medical practitioner.

While the above description refers to a motorized robotic arm, it should be understood that another arm or structure may be utilized to support the projector, the electric field sensor, the position tracking device, and/or the like. For example, a passive articulated arm secured to the ceiling of the operation room may be used. In this case, the configuration of the arm may be changed manually by a medical operator. The structure may even be a rolling floor table on which the projector, the electric field sensor, the position tracking device, and/or the like may be positioned.

In an embodiment in which commands are associated with air-wheel gestures, the diameter of the circle or semicircle performed during an air-wheel gesture may influence the command associated with the air-wheel gesture. For example, an air-wheel gesture having a first diameter may be associated with a first action to be executed while the same air-wheel gesture having a second and different diameter may be associated with a second and different action to be executed. In another embodiment, performing an air-wheel gestures with different diameter may trigger a same action to be executed but a characteristic of the action is dependent on the diameter of the air-wheel gesture. For example, if a zoom activity or a scroll activity is associated with an air-wheel gesture, the diameter of the air-wheel gesture may vary the sensitivity or the speed of the activity. For example, if a full turn of finger during an air-wheel gesture results in scrolling past 10 images, increasing the diameter of the air-wheel gesture would make a full turn of finger scroll past 20 images. Such a feature provides the system with additional precision and resolution in the actions to be executed.

Figure 11:
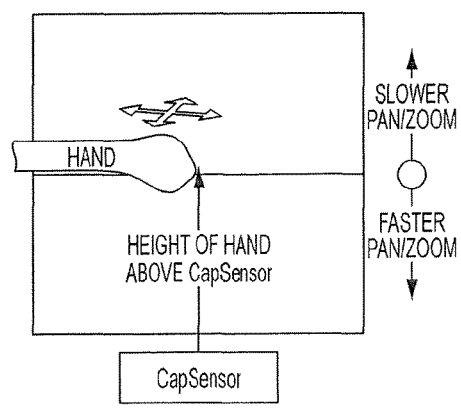
FIG. 11 illustrates an interaction with an electric field sensor being sensitive to a distance between a hand and its surface, in accordance with an embodiment.

In one embodiment, the electric field sensor is adapted to determine the distance between the object hold by the medical practitioner or the hand of the practitioner and the determined distance is transmitted to the controller along with the identified gesture. In this case, the determined distance may influence the action to be performed. In one embodiment, a given gesture performed at a first distance from the electric field sensor may be associated with a first action to be executed, such as zooming, while the same gesture performed at a second and different distance from the electric field may be associated with a different action to be executed, such as panning. In another embodiment, performing a given gesture at different distances from the electric field sensor may be associated with a same action to be executed but a characteristic of the action may depend on the distance between the hand of the medical practitioner and the electric field sensor, as illustrated in FIG. 11. In one embodiment, the electric field sensor determines the distance between its top surface and the hand of the practitioner or an object held by the practitioner while performing the gesture, and the determined distance may be used to vary the speed at which the action corresponding to the executed gesture. For example, the closer the hand of the medical practitioner is from the electric field sensor, the lower the speed of the corresponding action may be. For example, when the medical practitioner has selected the zooming mode of interaction, the medical practitioner may perform an air-wheel gesture in a plane substantially parallel to the surface of the electric field sensor in order to zoom in or out in a displayed image. If the air-wheel gesture is performed in proximity of the surface of the electric field sensor, the speed of the zooming may be less than the speed of the zooming resulting from an air-wheel gesture performed farther away from the surface of the electric field sensor. The same or reverse may apply for other actions to be executed such as panning.

In one embodiment, the electric field sensor may be adapted to detect to at least two different gestures performed substantially concurrently. For example, the electric field sensor may be adapted to detect concurrent translations and rotations of the object hold by the medical practitioner or the hand of the practitioner in order to detect combined gestures. For example, rotating the hand according to a rotation axis parallel to the surface of the electric field sensor may trigger the rotation of a displayed image while translating or swiping the hand in a plane substantially parallel to the surface of the electric may translate the displayed image. If the hand is concurrently translated and rotated, the displayed image is also concurrently rotated and translated.

Figure 12:
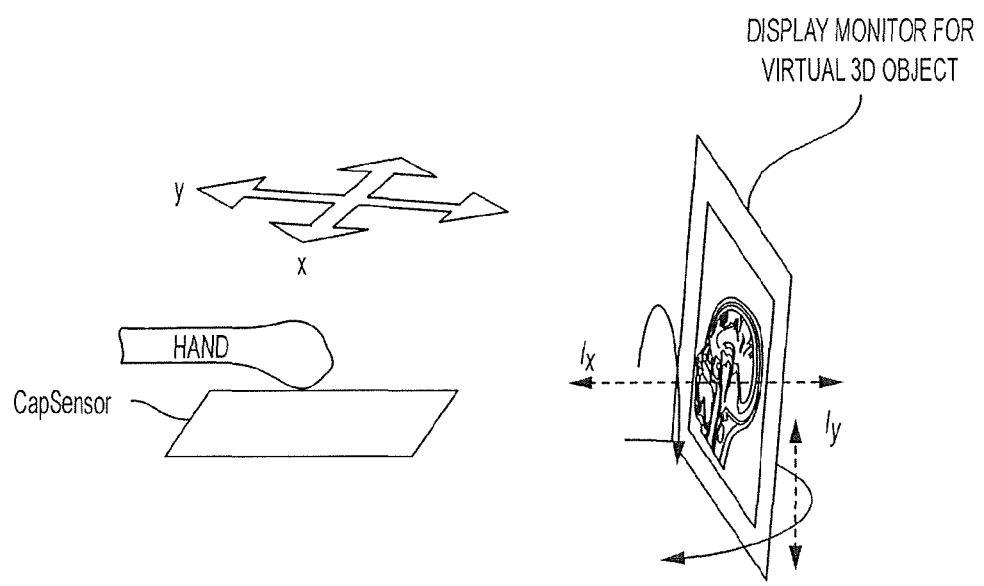
FIG. 12 illustrates a translation gesture for rotating a 3D image, in accordance with an embodiment.

In one embodiment, a translation gesture may be interpreted as a command for rotating a displayed image. As illustrated in FIG. 12, translating a hand along a given axis of the electric field sensor may be converted into a rotation of a displayed 3D image about a given axis. For example, translating a hand 5 cm in the x direction and 10 cm in the y direction would be interpreted by the controller as a 10 degrees rotation of the 3D image about the lx axis and a 20 degrees rotation of the 3D image about the ly axis, respectively.

In one embodiment, intuitive inertia may be added to 3D gestures. For example, an inertia effect may be added to air-wheel gesture control in order to scroll through large series of images or zooming in/out without too much physical effort. In one embodiment, three distinct modes may exist: 1) slow mode 2) fast mode 3) inertial mode.

The slow mode is activated when the speed of air-wheel gesture is below a given threshold. In this mode, raw air-wheel input from practitioner is directly translated to scroll or zoom commands for accurate 1 to 1 control of the image set. If the air-wheel is executed at a speed above the given threshold, the fast mode is activated. Slow scroll enables practitioner to navigate an image-set frame by frame.

In the fast mode, as long as the medical practitioner executes an air-wheel gesture at a speed that is greater than the given threshold, multiple image-set scrolling or faster zooming occurs. However, once the medical practitioner stops the air-wheel gesture, the scrolling or zooming action does not stop, unlike in the slow scroll mode. Instead the inertial mode is activated.

Before the inertial mode be activated, the latest speed at which the medical practitioner executed the air-wheel gesture is recorded. The recorded speed is then used as an input to calculate the "kick", or initial velocity, that the automatic air-wheel will receive for inertial scrolling. Once the inertial mode is activated, the system is made to continue zooming/scrolling even when no input from user is received. An elastic rubber band effect is emulated during inertial mode for smooth experience, where automatic air-wheel is fast initially, and decelerates slowly to a stop over a predefined period of time.

In one embodiment and as described above, the system may comprise a speaker controlled by the controller for providing an audio feedback to the medical practitioner who operates the electric field sensor. The audio feedback may provide the medical practitioner with an easy reference to navigate through various menus. When a particular gesture is successfully recognized by the controller, a unique and respective audio cue (e.g. a beep or series of beeps) intimates the practitioner of this change in system state. This may allow the medical practitioner to use the electric field sensor without ever needing to take their eyes off the display monitors.

In one embodiment, the system may comprise a microphone connected to the controller and a medical practitioner may input voice commands via the microphone in addition to the commands generated via the gestures detected by the electric field sensor. For example, the medical practitioner may say "scroll" in order to activate the scroll mode and then use and air-wheel gesture to scroll through images or the like.

Figure 13:
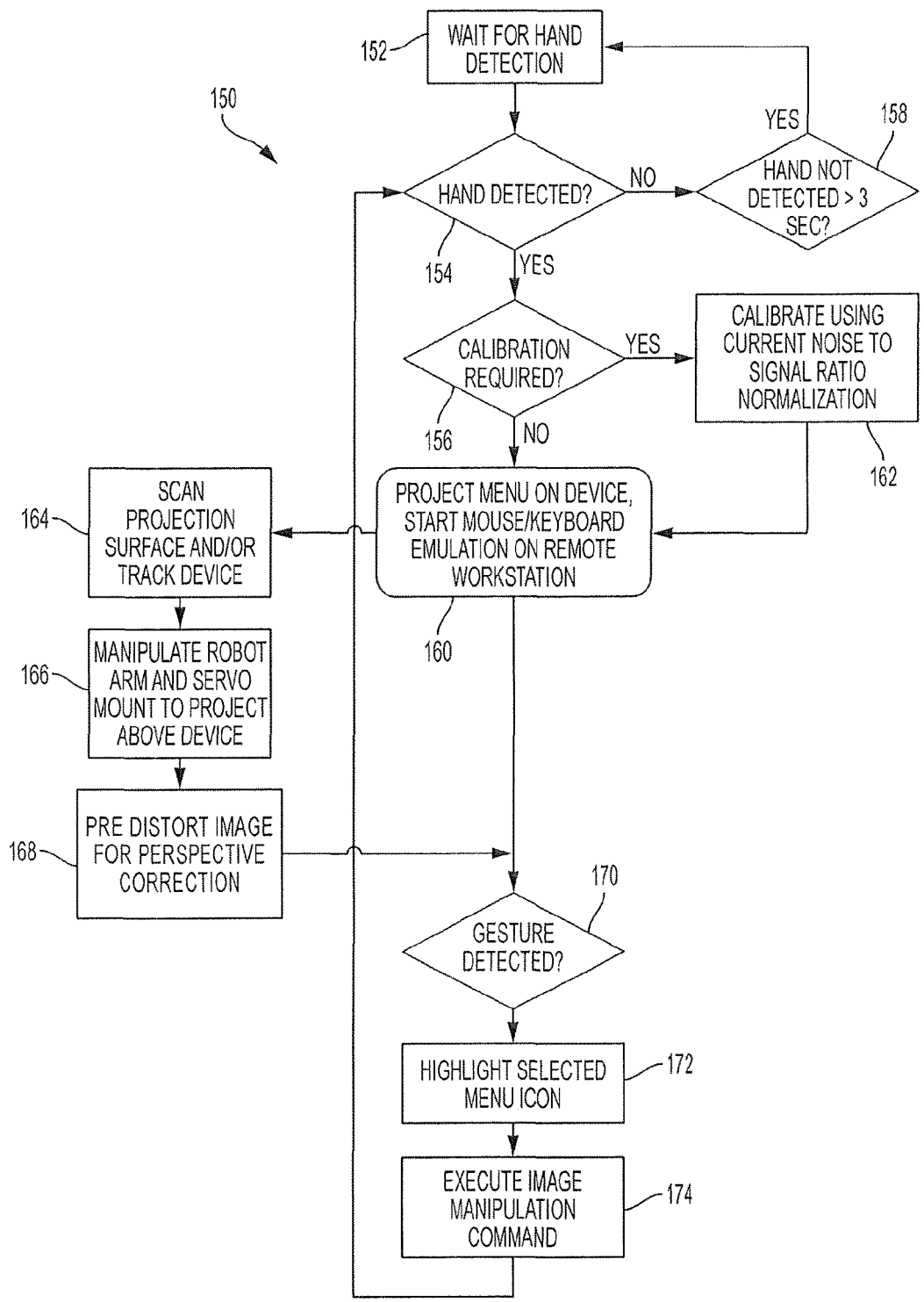
FIG. 13 is a flow chart illustrating a method for allowing a medical practitioner to interact with medical data, in accordance with an embodiment.

FIG. 13 illustrates one embodiment of a method 150 for allowing a medical practitioner to interact with medical data such as a medical image. It should be understood that the method 150 is implemented using the system 10, 50.

At step 152, the controller is in stand-by and waits for the detection of a gesture by the electric field sensor. At step 154, the controller determines whether a gesture has been detected by the electric field gesture. If a gesture is detected, the controller determines whether a calibration is required at step 156. In one embodiment, the electric field sensor receives both high and low frequency signals from electrodes. The high frequency signals usually correspond to electrical noise in the system. It is determined that a calibration is required when noise to low frequency signal ratio is greater than a predefined threshold. If no gesture is detected, the duration of the period during which no gesture has been detected is compared to a time duration threshold at step 158. If the duration during which no gesture has been detected is equal to or less than the time duration threshold, then the method returns to step 152. If the duration during which no gesture has been detected is greater than the time duration threshold, step 156 is executed.

If the controller determines that no calibration is required, the controller projects a menu image on the electric field sensor and starts a mouse emulation on a remote workstation at step 160, i.e. the controller starts sending commands that correspond to mouse commands upon detection of corresponding gestures. If the controller determines that a calibration is required, a calibration is performed using current noise to signal ratio normalization.

At step 164, the positon of the electric field sensor is tracked using a position tracking device. Optionally, the projection surface may also be scanned by the position tracking device or any other adequate device such as an IR Depth camera, a stereo camera system, or the like. The scan of the projection image allows determining any irregularities on the projection surface such as portions of the projection surface that are not orthogonal to the projector axis.

At step 166, the controller manipulates the robotic arm in order to position the projector above the electric field sensor. At step 168, the controller pre-distorts the image to be displayed for perspective correction. By pre-distorting the image, it is possible to modify the image projected by the projector so that the projected image appears normal even if the projection surface presents irregularities.

When it determines that a gesture has been detected by the electric field sensor at step 170, the controller commands the projector to project the menu image on the electric field sensor. At step 172, the controller commands the projector to highlight the menu icon that corresponds to the mode of interaction selected by the medical practitioner by performing the detected gesture. At step 174, the controller executes the command associated with the detected gesture such as a given manipulation of a displayed medical image. Then the method returns to step 154.

In one embodiment, a first set of some gestures is to be used in order to select a given mode of operation such as the zoom mode, the pan mode, etc. Once the given mode of operation has been selected, a second set of icons gestures may be used to interact with the medical information. In one embodiment, the first and second sets of gestures are different so that no gesture present in the first set can be contained in the second set. In another embodiment, a same gesture may be contained in both the first and second sets of gestures. In this case, a given gesture may be used to activate a given mode of operation, and once the given mode of operation has been activated, the same gesture may be used to perform a different action, such as zooming in, for example.

In one embodiment, the projector may be adapted to display a first set of menu icons each corresponding to a given mode of operation of the system. Once a given mode of operation has been activated using a corresponding gesture, the projector may be adapted to project a second set of menu icons each corresponding to a respective interaction with the medical data within the selected mode of operation. In one embodiment, once the given mode of operation has been activated, the first set of icons may no longer be projected and only the second set of icons is projected. In another embodiment, both sets of icons are concurrently displayed once the given mode of operation has been activated The following provides an exemplary vocabulary for gestures based on palm-down horizontal hand motions and single-finger movement:

Fist/Finger: Moves the mouse cursor on the screen.
Single Air Tap: Region and system state sensitive.
Double Air Tap: Reset image
Left Swipe: Activate zoom mode
Right Swipe: Activate scroll mode
Up Swipe: Activate pan mode. Pan by moving cursor to a desired location using one finger.
Down Swipe: Activate window level mode. The display surface is divided into four quadrants for example, each representing a pre-set window level. Hovering above a particular quadrant selects a desired image brightness and contrast.

It should be understood that combinations of the above-presented exemplary gestures and/or variations of these exemplary gestures may be used.

In one embodiment, the above described system and method for interacting with medical data allows for intuitive and ergonomic touchless interactions with medical images in a sterile environment, with specific attention to real-life requirements and constraints of a surgical/interventional environment.

In one embodiment, using electric field sensing requires substantially less processing power and operates independently of its surrounding's lighting conditions. These features ensure that an object of interest may be tracked robustly with little risk of failures and errors. Such reliable tracking of a practitioner's hand in real-time also allows for detection and implementation of several novel ergonomic gestures, for example:

In one embodiment, the present system allows the medical practitioner to interact with the medical information independently of the lighting conditions in which the system is used. Since, the operation of the electric field sensor is independent on the lighting conditions, it is possible to interact with the medical information even in the dark, for example.

In one embodiment, the present system and method make it easy for a novice user to quickly pick up and get comfortable with the system. The natural and easy to remember gestures ensure a very small learning curve for a new user. Within just a few minutes of using the present system, a practitioner can get comfortable enough to use it without breaking his/her line of sight with monitors on which medical images are displayed.

In one embodiment, the electric field sensor is used in a non-contact manner or touchlessly. This allows reducing any risk of transferring any contaminants that could be present on the surface of the electric field sensor.

In one embodiment, the electric field sensor may be operated even when its field of view is obstructed by an object. For example, the electric field sensor is operable even when it is covered by a surgery drape.

While in the above description an electric field sensor is used for detecting a gesture performed by a medical practitioner and only displaying medical information according to the gesture, the following presents a system for further providing the medical practitioner with a visual feedback on its interaction with a sensor.

Figure 14:
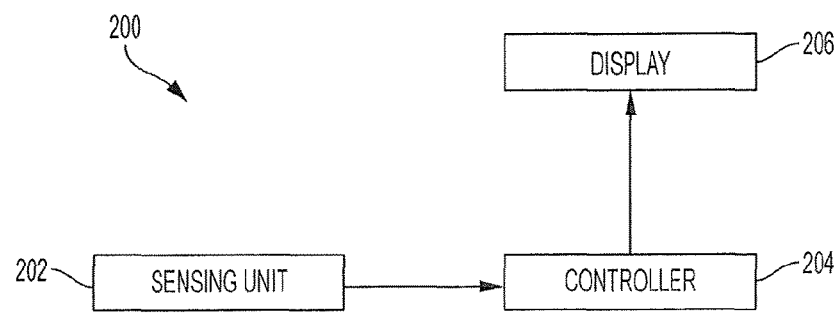
FIG. 14 is a block diagram of a system for allowing a medical practitioner to interact with medical information and providing a visual feedback to the medical practitioner, in accordance with an embodiment.

FIG. 14 illustrates one embodiment of a system 200 for interacting with medical data, such as medical images, and providing a user, such as a medical practitioner, with a visual feedback on its interaction with the system 200. The system 200 comprises at least a sensing unit 202, a controller 204 and a display unit 206. The sensing unit 202 is adapted to detect a gesture performed by the medical practitioner who uses the system 200. As described above, the medical practitioner may use one of his hands or an object to interact with the sensing unit 202. The sensing unit 202 is further adapted to detect the position and orientation of the hand or the object used by the medical practitioner.

The controller 204 is adapted to execute a command according to the gesture detected by the sensing unit 202 and display medical information on the display unit 206, as described above. The controller 204 is further adapted to generate a graphical user interface (GUI) and display the generated GUI on the display unit 206 such as on the same screen on which the medical data is displayed. The GUI provides the medical practitioner with a visual feedback on its interaction with the sensing unit 202.

In one embodiment, the GUI comprises at least one icon each corresponding to a respective command to be executed upon the detection of a respective gesture. The GUI further comprises a graphical or virtual object for representing the hand or the object used by the medical practitioner to interact with the sensing unit 202. For example, the graphical object may correspond to an arrow. The position of the graphical object relative to the icons in the GUI is chosen as a function of the position of the hand or object used by the medical practitioner. In one embodiment, the position of the graphical object relative to the icons in the GUI is chosen as a function of the 3D position of the hand or object used by the medical practitioner. In one embodiment, the position of the graphical object relative to the icons in the GUI is chosen as a function of the position of the hand or object used by the medical practitioner relative to the sensing unit 202.

It should be understood that determining the position of the hand or the object may correspond to determining the position of a single point of the hand or the object. For example, the position of the hand may be determined by knowing the position of a fingertip. In another example, the position of a pen may be determined knowing the position of the end of the pen opposite to the hand holding the pen.

The orientation of the graphical object relative to the icons in the GUI is also chosen as a function of the orientation of the hand or object used by the medical practitioner relative to the sensing unit 202.

In one embodiment, when the surgeon is busy with the delicate work of surgery, interacting with medical images should not interrupt this delicate surgical workflow. Therefore, the surgeon cannot keep looking at the position of his hand relative to the sensing unit 202 and go back/forth between his hand and the display unit 206 on which the medical data is displayed. When the GUI provides the surgeon with a visual feedback of the relative position between his hand and the sensing unit and the orientation of his hand, the surgeon's gaze remains on the display and he does not need to look at his hand or the sensing unit 202 for interacting with the system 200.

In one embodiment, the position and orientation of the object used by the medical practitioner are monitored substantially continuously so that the position and orientation of the graphical object be updated in the GUI in substantially real time.

Figure 15:
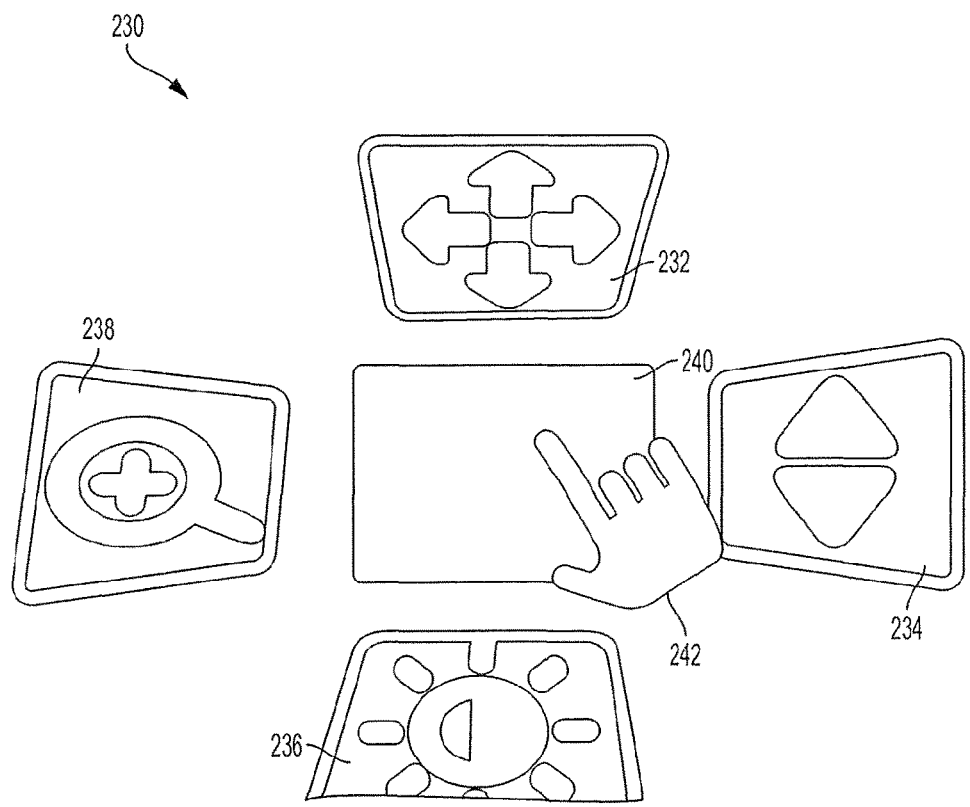
FIG. 15 illustrates an exemplary graphical user interface to be displayed along with medical data, in accordance with an embodiment.

In one embodiment, the GUI further comprises a graphical or virtual representation of the sensing unit 202, hereinafter referred to as the graphical sensing unit. In this case, the icons are each positioned at a respective location relative to the graphical sensing unit within the GUI. For example, the icons may be positioned over the graphical sensing unit or around the graphical sensing unit. FIG. 15 illustrates an exemplary GUI 230 which comprises four icons 232, 234, 236 and 238 which each correspond to a respective mode of operation, a graphical sensing unit 240 and a virtual hand 242 for presenting the hand of the medical practitioner. The position of the icons 232-238 and that of the graphical sensing unit are fixed within the GUI 230 while the position and orientation of the virtual hand 242 is adjusted within the GUI as a function of the hand position and orientation of the hand of the medical practitioner. This allows the medical practitioner to know the position of his hand relative to the sensing unit 202 while only looking at the display unit 206 where the medical data is displayed without needing to look at his hand or the sensing unit 202.

In one embodiment, the controller 204 uses object recognition to determine the object used by the medical practitioner to interact with the sensing unit 202. In this case, the graphical object representing the object used by the medical practitioner may be a graphical representation of this object. For example, if the medical practitioner uses one of his fingers to interact with the sensing unit 202, the controller 204 may generate a graphical representation of a closed fist with a finger sticking out to represent the hand of the medical practitioner. If the medical practitioner uses a pen to interact with the sensing unit 202, the controller 204 may generate a graphical representation of a pen and display this graphical representation within the GUI. In one embodiment, the system 200 comprises a database containing predefined virtual objects and the controller 204 is adapted to select a given one of the predefined virtual objects according to the performed object recognition. The controller 204 may the virtual object of which the shape matches that of the real object.

Figure 16:
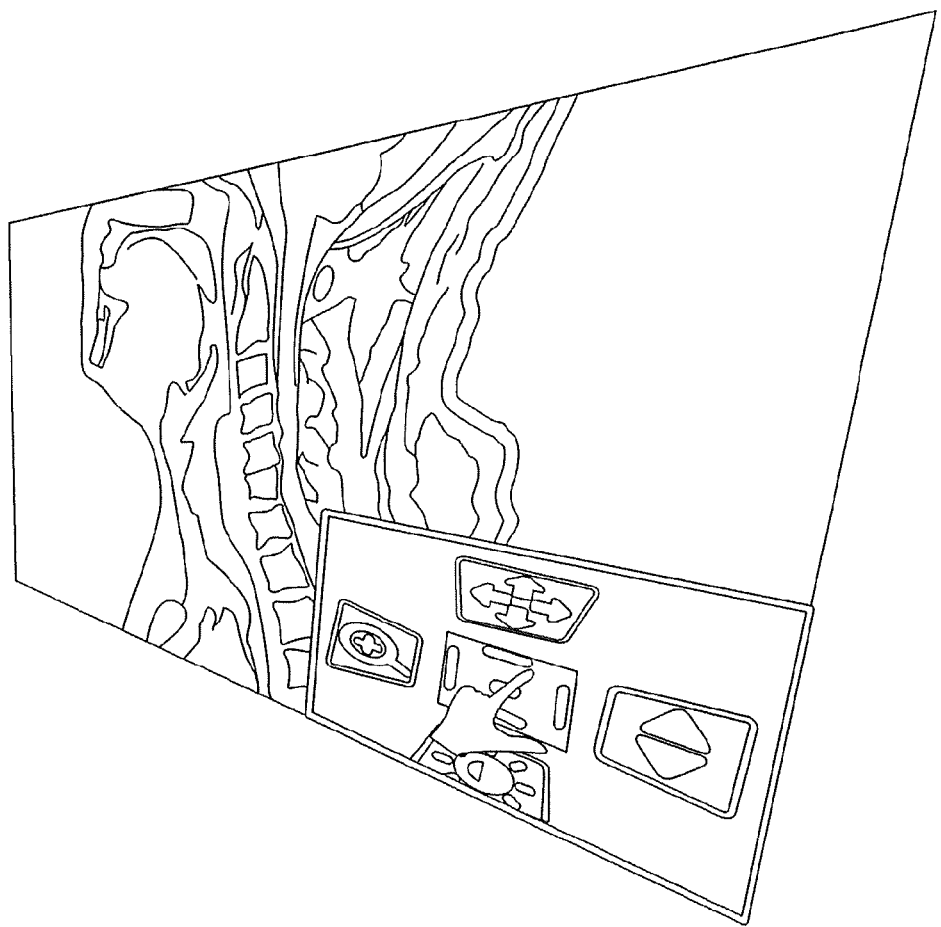
FIG. 16 illustrates the display of a medical image and an overlay graphical user interface, in accordance with an embodiment.

In one embodiment, the GUI is displayed adjacent to the medical data on the same display unit. In this case, the screen of the display unit 206 may be divided into two sections, i.e. a first section for displaying the medical data such as a medical image, and a second section for displaying the GUI. In another embodiment, the GUI corresponds to an overlay GUI which is displayed over the displayed medical data as illustrated in FIG. 16.

In one embodiment, the sensing unit 202 comprises a single sensor to determine both the gestures performed by the medical practitioner and the position and orientation in space of the object used by the medical practitioner for interacting with the medical data. For example, the single sensor may be an optical sensor such as a camera. In another embodiment, the single sensor may comprise an ultrasonic sensor array combined with wearable inertial measurement units (IMU's) for gesture recognition and determination of the position and orientation of the hand or object. In this case, gestures performed by the medical practitioner are determined by the controller 206 using the data acquired by the sensor such as images acquired by a camera. The controller 204 then determines the commands corresponding to the gestures and display medical data on the display unit 206 according to the commands. The controller 204 is further adapted to display a virtual representation of the object used for interacting with the system 200 within the GUI displayed on the display unit 206. In this embodiment, a camera such as a 3D camera, a stereo camera system comprising at least two cameras, a time-of-flight camera or the like may be used. It should be understood that any adequate optical sensor adapted to receive and detect light from the environment and interpret the detected light into 2D or 3D information to allow detection of a gesture and the position and orientation of a hand of object may be used.

In one embodiment and as described above, icons are displayed on a reference surface that is imaged by the camera. For example, a projector may display the icons on the reference surface as described above. In another embodiment, the reference surface may comprise a screen on which the icons are displayed. The displayed icons each correspond to a respective icon contained in the GUI. In one embodiment, the relative position between the icons contained in the GUI corresponds to the relative position between the icons that are displayed on the reference surface.

Figure 17:
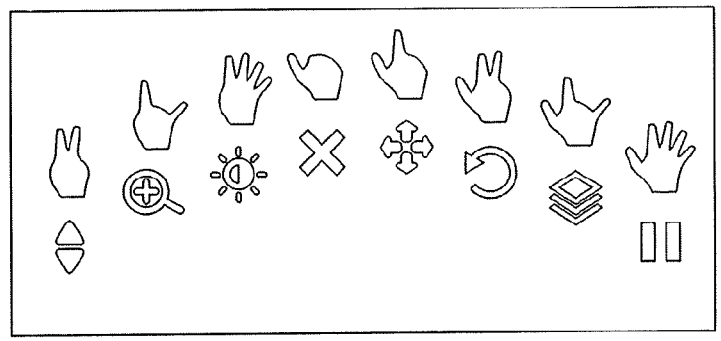
FIG. 17 illustrates exemplary static gestures, in accordance with an embodiment.

In another embodiment, the sensing unit 202 uses the fusion between two different sensors for determining the gestures performed by the medical practitioner and the position and orientation of the hand or object used by the medical practitioner. A first sensor is used for detecting the position of the hand or object used by the medical practitioner while the second sensor is used for the detection of the orientation of the hand or object. For example, the sensing unit 202 may comprise an electric field sensor for detecting the position and an optical sensor such as a camera is used for imaging the hand or object in order to determine its orientation. It should be understood that any adequate method for determining the orientation of the hand or object from the images taken by the optical sensor may be used. A camera such as such as a 2D camera, a monochrome camera, a stereo camera, a time-of-flight camera or the like may be used. The gestures can be detected by the first and/or second sensor. In one example, the position of the hand or object used by the medical practitioner for interacting with the sensing unit 202 is determined from the data acquired by an electric field sensor which measures the position of the fingertip or the end of the object held by the medical practitioner while the orientation of the object is determined using the images acquired by a camera. The gestures may be determined using the electric field sensor and/or the camera. For example, static gestures such as the gestures illustrated in FIG. 17 may be determined using the images acquired by the camera while at least some dynamic gestures may be determined using the data acquired by the electric filed sensor. It should be understood that at least some dynamic gestures may also be determined using the images acquired by the camera.

Figure 18:
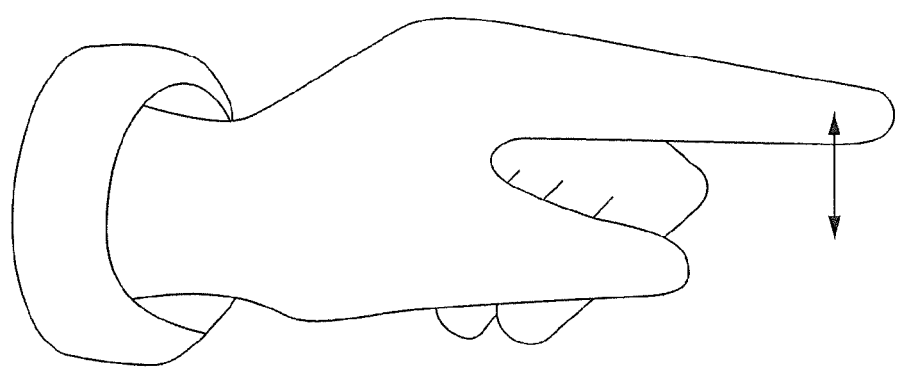
FIG. 18 illustrates an exemplary finger tapping gesture, in accordance with an embodiment.

FIG. 18 illustrates one embodiment of a dynamic gesture which may be detected by an adequate camera. The illustrated dynamic gesture corresponds to a finger tapping. In order to perform the finger tapping, the medical practitioner extends his index finger and moves the tip up and down to simulate a tap on a button. The medical practitioner may also extend his thumb and tap his index finger on its thumb in order to 'feel' like a button. Such as dynamic gesture may be interpreted by the controller 204 as a mouse click command.

It should be understood that, when a camera is used in connection with an electric field sensor, the camera is positioned so as to image the electric field sensor or a region above the electric field sensor in which the reference object, e.g. the hand of the medical practitioner or the object used by the medical practitioner, is present.

In one embodiment, the size and/or position of the GUI displayed on the display unit 206 is adjustable. For example, using adequate gestures, the medical practitioner may input a command to move the GUI to another location within the screen, increase or decrease the size of the GUI, and/or suppress the display of the GUI.

While the above description refers to a display unit comprising a single screen on which both medical information/data and a GUI are displayed, the person skilled in the art will understand that the display unit may comprise more than one screen. For example, the display unit may comprise a first screen on which the medical information such as a medical image is displayed and a second and separate screen on which the GUI is displayed. In this case, the relative position between the two screens and the dimension of the screens are chosen so that the GUI displayed on the second screen be in the field of view of the medical practitioner while he is looking at medical information displayed on the first screen of the display unit. This may be achieved by having the second by positioning the second screen adjacent to the first screen so that the second screen be within the field of view of the medical practitioner while he is looking at the first screen. For example, the second screen may in physical contact with the first screen and positioned below the first screen. The second screen may be chosen to be smaller than the first screen.

It should be understood that the first and second screens may be part of a single display devices. Alternatively, the first and second screens may each be part a respective display devices so that the display unit comprises two separate display devices.

Figure 19:
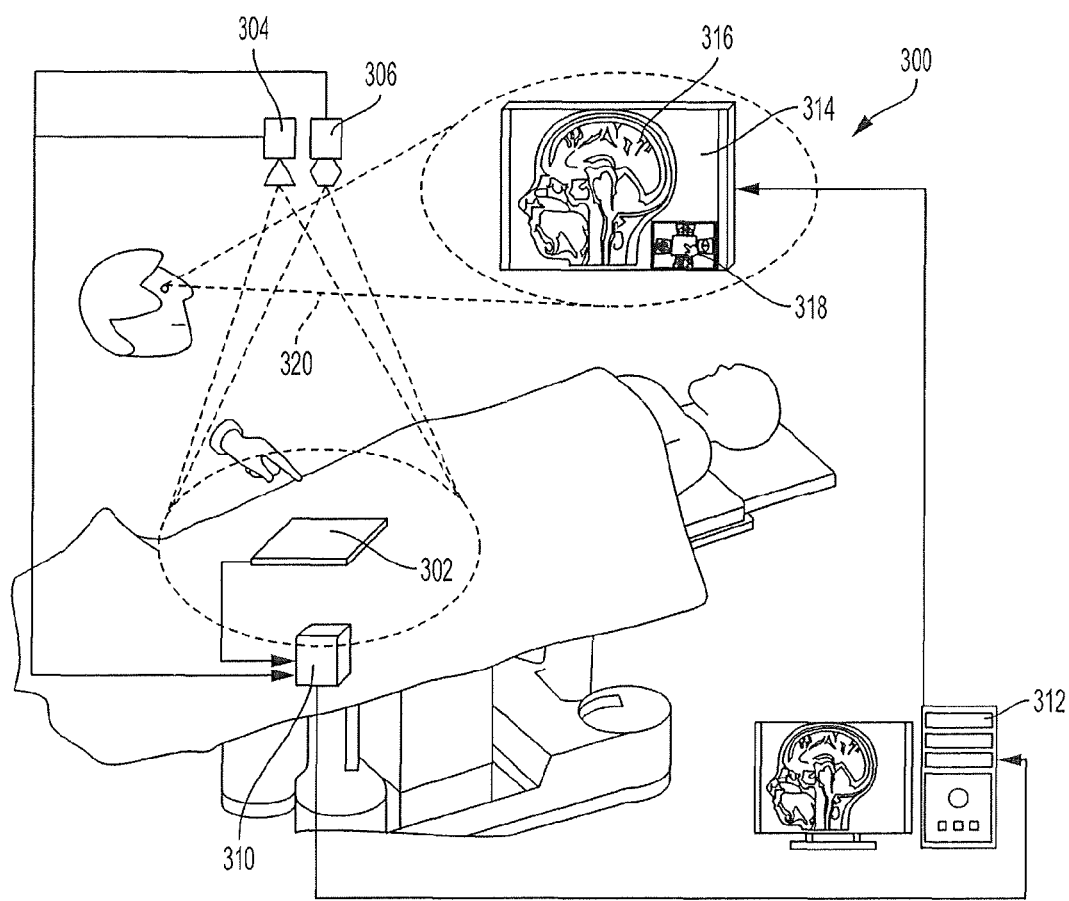
FIG. 19 illustrates a system for interacting with medical information, comprising a single display device for displaying thereon both medical information and an overlay GUI, in accordance with an embodiment.

FIG. 19 illustrates an exemplary system 300 adapted to display a GUI and a medical image on the same screen. The system 300 comprises an electric field sensor 302, a camera 304, a projector 306 for projecting icons, a controller 310, a computer machine 312 and a single display device 314. The controller 310 is in communication with the electric field sensor 302, the camera 304, the projector 306 and the computer machine 312.

The controller 310 is adapted to receive images taken from the camera 304 and determine at least the orientation of the hand of the medical practitioner from the received images. The controller 310 is further adapted to receive the position in time of the fingertip of the medical practitioner from the electric field sensor 302 and determine the gesture performed by the medical practitioner from the received position of the fingertip. The controller 310 is further adapted to generate a GUI in substantially real-time. The GUI comprises four virtual icons and a virtual representation of the hand of the medical practitioner. The position of the virtual representation of the hand within the GUI is determined using the position of the fingertip received from the electric field sensor 302. The orientation of the virtual representation of the hand within the GUI is determined according to the determined orientation of the hand obtained from the images received from the camera 304.

After creating the GUI, the controller 310 transmits the GUI to the computer machine 312 which is in charge of displaying the medical information on the display device 314. It should be understood that the controller 310 also transmits any detected gesture to the computer machine which retrieves the command that corresponds to the detected gesture and executes the command. Alternatively, the controller 310 may be adapted to determine the command that corresponds to the detected gesture and then transmits the command to the computer machine which executes the command.

In the illustrated embodiment, the computer machine 312 is adapted to display both the medical image 316 and the overlay GUI 318 on the same display device 314. In the illustrated example, the overlay GUI 318 is displayed over the medical image 316 at the right bottom corner of the screen of the display device 314. The person skilled in the art will understand that other configurations are possible.

As a result of the display of the medical image and the GUI on the same display device, the GUI is always in the field of view 320 of the medical practitioner while he is looking at the screen of the display device 314 to see the medical information displayed thereon.

In one embodiment GUI is updated in real time so that the position and orientation of the virtual hand substantially always correspond to these of the real hand.

Figure 20:
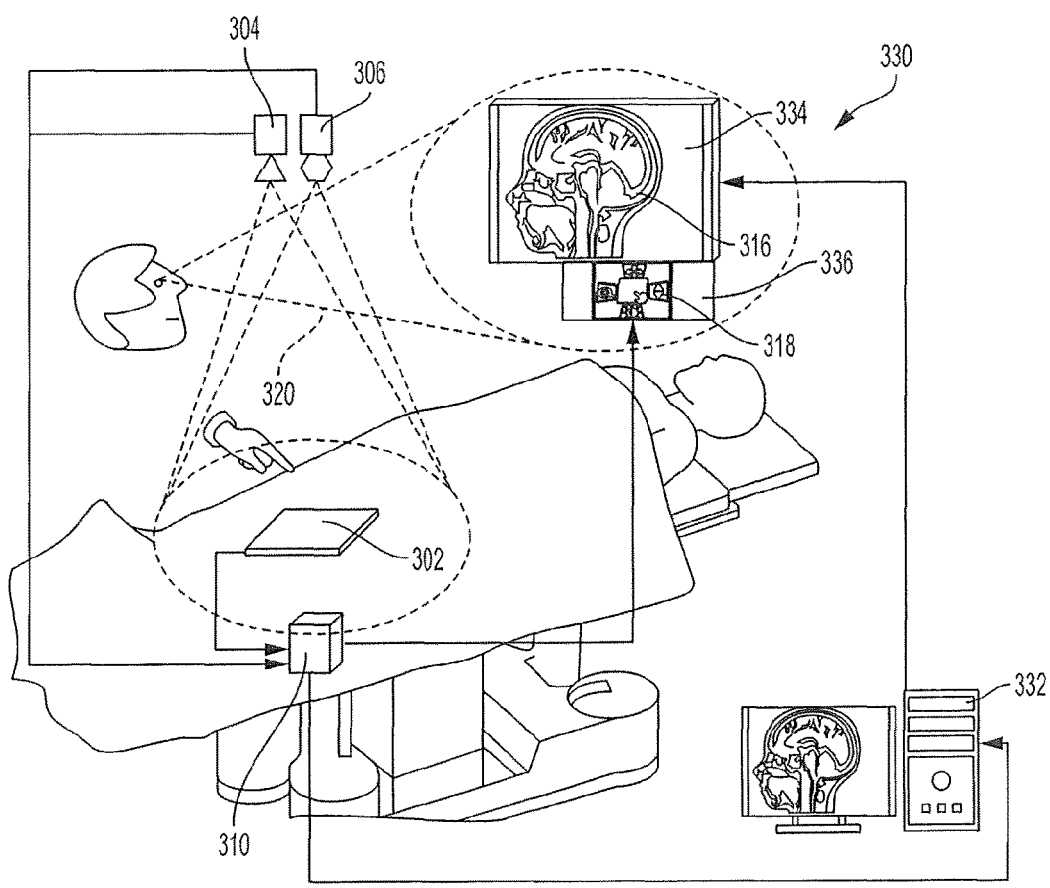
FIG. 20 illustrates a system for interacting with medical information, comprising two separate display device for displaying medical information and a GUI, in accordance with an embodiment It will be noted that throughout the appended drawings, like features are identified by like reference numerals.

While the system 300 comprises a single display device 314, FIG. 20 illustrates an embodiment of a system 330 that comprises two separate display devices. The system 330 comprises the same camera 304, projector 306, electric field sensor 302 and controller 310 as those contained in the system 300. The system 330 further comprises a computer machine 332, a first or main display device 334 and a second or auxiliary display device 336.

The computer machine 332 is adapted to display the medical image 316 on the screen of the first display device 334 and the GUI 318 on the screen of the second display device 336. The position of the second display device 336 relative to the first display device 334 is chosen so that the GUI 318 be contained in the visual field of view 320 of the medical practitioner while he is looking at the medical image 316. This can be achieved by adequately choosing the size of the screen of the second display 336 and positioning the second display device 336 adjacent to the first display device 334. For example, the second display device 336 may be in physical contact with the first display device 334. It should be understood that the relative position between the first and second display devices 334 and 336 illustrated in FIG. 20 is exemplary only.

It should be understood that any adequate type of display device may be used for displaying the medical information/data and the GUI. For example, light-emitting diode displays, liquid crystal displays and/or the like may be used.

While in the above description, the GUI comprises at least a virtual representation of the object used by the medical practitioner to interact with the sensing unit 202 and at least one virtual icon, it should be understood that other configurations may be possible. For example, the GUI may further comprise a virtual representation of the sensing unit 202 or an element of the sensing unit 202 such as a virtual representation of an electric field sensor when the sensing unit 202 comprises both a camera and an electric field sensor. In another example, the GUI may only comprise a virtual representation of the object used by the medical practitioner to interact with the sensing unit 202 and a virtual representation of the sensing unit 202 or a component of the sensing unit such as a virtual representation of an electric field sensor when the sensing unit 202 comprises both a camera and an electric field sensor. In this case, the GUI comprises no virtual icons and the position of the virtual representation of the object relative to the virtual representation of the sensing unit is determined according to the position of the object determined by the sensing unit 202.

While in the above description, the sensing unit 202 is adapted to detect both the position and orientation of the object used by the medical practitioner to interact with the sensing unit 202, it should be understood that the sensing unit 202 may be adapted to detect only the position of the object. In this case, the position of the virtual representation of the object in the GUI is determined using the position of the object relative to the sensing unit 202 determined by the sensing unit 202 and the orientation of the object is not represented in the GUI.

It should be understood that the GUI may correspond to a 2D representation of the object and the icons and/or the sensing unit when the sensing unit is adapted to detect only the position of the object. When the sensing unit is adapted to determine both the position and orientation of the object relative to the sensing unit, the GUI may comprise a 3D virtual representation of the object.

While in the above description and figures, the sensing unit is represented positioned on a bed, it should be understood that this particular position for the sensing unit is exemplary only and that the sensing unit may be positioned at any adequate position such as on a table adjacent to the bed for example. In one embodiment, the sensing unit may be a handheld device that may be hold by the medical practitioner and positioned on a surface such as on a bed when needed.

It should be understood that wired or wireless communication may be used for connecting the different elements of the above-described system.

The embodiments of the invention described above are intended to be exemplary only. The scope of the invention is therefore intended to be limited solely by the scope of the appended claims.

The invention claimed is:

1. A system for permitting a medical practitioner to interact with medical information, the system comprising:
at least one touchless sensor for detecting at least a 3D position of a reference object used by the medical practitioner to touchlessly interact with the at least one touchless sensor; and
at least one control unit being in communication with the at least one touchless sensor for:
determining a touchless gesture performed by the medical practitioner using the 3D position of the reference object detected by the at least one touchless sensor;
identifying a command relative to the medical information that corresponds to the received touchless gesture and executing the command in order to display the medical information on a display unit;
generating a graphical user interface (GUI) comprising a virtual representation of the reference object, a virtual representation of the at least one touchless sensor, and a virtual representation of at least one virtual icon, a position of the virtual representation of the reference object relative to the virtual representation of the at least one touchless sensor within the GUI being chosen as a function of the 3D position of the reference object detected by the at least one touchless sensor so as to provide the medical practitioner with a visual feedback of a relative position between the reference object and the at least one touchless sensor, each of the at least one virtual icon corresponding to one of a respective mode of operation, a respective user notification and a respective system setting option; and
displaying the GUI on the display unit along with the medical information;
wherein displaying the GUI comprises displaying the virtual representation of the at least one sensor at a location spaced apart from a sensing region of the at least one touchless sensor.

2. The system of claim 1, wherein the display unit comprises first and second display devices, and wherein the controller is configured for displaying the medical information on the first display device and the GUI on the second display device.

3. The system of claim 2 wherein the first and second display devices are positioned adjacent to one another so that the GUI and medical information are in the field of view of the medical practitioner when the medical practitioner looks at the displayed medical information.

4. The system of claim 1 wherein the display unit comprises a single display device and wherein the displayed GUI occupies a portion of an image comprising the displayed medical information.

5. The system of claim 1, wherein the at least one touchless sensor is further adapted to detect an orientation of the reference object, an orientation of the virtual representation of the reference object within the GUI being chosen as a function of the orientation of the reference object detected by the at least one touchless sensor.

6. The system of claim 5, wherein the at least one touchless sensor comprises a single sensor adapted to determine the 3D position and the orientation of the reference object and determine the touchless gesture performed by the medical practitioner.

7. The system of claim 5, wherein the at least one touchless sensor comprises a first sensor for determining the 3D position of the reference object and a second sensor for determining the orientation of the reference object, the touchless gesture being determined by one of the first and second sensors.

8. The system of claim 7, wherein the first sensor comprises an electric field sensor for determining the 3D position of the reference object and the second sensor comprises an optical sensor for determining an orientation of the reference object.

9. The system of claim 8, wherein the optical sensor comprises a camera, the camera comprising one of a 2D camera, a monochrome camera, a stereo camera and a time-of-flight camera.

10. The system of claim 1, wherein the reference object comprises a body part of the medical practitioner.

11. The system of claim 1, wherein the reference object is made of one of a conductive material and a semi-conductive material.

12. The system of claim 1, wherein the medical information comprises a medical image, a 3D model, and any combination or sequence thereof.

13. The system of claim 1, wherein the command relative to the medical information comprises a command that causes a change of at least one characteristic of an already displayed medical image.

14. A computer-implemented method for allowing a medical practitioner to interact with medical information, the method comprising:
   detecting a 3D position of a reference object used by the medical practitioner to touchlessly interact with at least one touchless sensor based on output from at least one touchless sensor;
   determining a touchless gesture performed by the medical practitioner using the detected 3D position of the reference object;
   identifying a command relative to the medical information that corresponds to the received touchless gesture and executing the command in order to display the medical information on a display unit;
   generating a graphical user interface (GUI) comprising a virtual representation of the reference object, a virtual representation of the at least one touchless sensor, and a virtual representation of at least one virtual icon, the position of the virtual representation of the reference object relative to the virtual representation of the at least one touchless sensor within the GUI being chosen as a function of the detected 3D position of the reference object detected by the at least one touchless sensor so as to provide the medical practitioner with a visual feedback of a relative position between the reference object and the at least one touchless sensor, each of the at least one virtual icon corresponding to one of a respective mode of operation, a respective user notification and a respective system setting option; and
   displaying the GUI on the display unit along with the medical information;
   wherein displaying the GUI comprises displaying the virtual representation of the at least one sensor at a location spaced apart from a sensing region of the at least one touchless sensor.

15. The computer-implemented method of claim 14 wherein displaying the medical information and displaying the GUI comprise displaying the medical information and GUI on first and second separate display devices.

16. The computer-implemented method of claim 15 wherein the first and second display devices are positioned adjacent to one another so that the GUI and medical information are in the field of view of the medical practitioner when the medical practitioner looks at the displayed medical information.

17. The computer-implemented method of claim 14 wherein wherein displaying the medical information and displaying the GUI comprise displaying the medical information and GUI on the same display device, wherein the displayed GUI occupies a portion of an image comprising the displayed medical information.

18. The computer-implemented method of claim 14, further comprising detecting an orientation of the reference object.

19. The computer-implemented method of claim 18, wherein said at least one touchless sensor comprises a first sensor and a second sensor and wherein detecting the 3D position of the reference object is performed using output from the first sensor and said detecting the orientation of the reference object is performed using output from the second sensor, the touchless gesture being determined using at least one of the first and second sensors.

20. The computer-implemented method of claim 19, wherein the first sensor comprises an electric field sensor for determining the 3D position of the reference object and the second sensor comprises an optical sensor for determining the orientation of the reference object.

* * * * *